US008945582B2

(12) United States Patent
De Hemptinne et al.

(10) Patent No.: US 8,945,582 B2
(45) Date of Patent: Feb. 3, 2015

(54) VACCINE

(75) Inventors: Herve De Hemptinne, Rixensar (BE); Michel Duchene, Rixensart (BE); Anne Mary, Rixensart (BE); Marc Sonveaux, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 1267 days.

(21) Appl. No.: 12/440,054

(22) PCT Filed: Sep. 7, 2007

(86) PCT No.: PCT/EP2007/059390
§ 371 (c)(1),
(2), (4) Date: Mar. 5, 2009

(87) PCT Pub. No.: WO2008/028956
PCT Pub. Date: Mar. 13, 2008

(65) Prior Publication Data
US 2010/0034850 A1  Feb. 11, 2010

(30) Foreign Application Priority Data

Sep. 7, 2006 (GB) .................................. 0617602.8
Dec. 21, 2006 (GB) .................................. 0625593.9

(51) Int. Cl.
*A61K 39/295* (2006.01)
*A61K 39/13* (2006.01)
*A61K 39/116* (2006.01)
*A61K 39/00* (2006.01)
*A61K 39/12* (2006.01)

(52) U.S. Cl.
CPC ............. *A61K 39/13* (2013.01); *A61K 39/0018* (2013.01); *A61K 39/12* (2013.01); *A61K 2039/5252* (2013.01); *C12N 2770/32634* (2013.01); *C12N 2770/2671* (2013.01); *A61K 2039/55505* (2013.01); *A61K 2039/55544* (2013.01); *C12N 2730/10134* (2013.01)
USPC .................. 424/201.1; 424/203.1; 424/204.1; 424/217.1

(58) Field of Classification Search
CPC . A61K 39/00; A61K 39/12; A61K 2039/545; A61K 2039/55505; A61K 2039/55544; A61K 2039/70; A61K 39/0018; A61K 39/099; A61K 39/13
See application file for complete search history.

(56) References Cited

U.S. PATENT DOCUMENTS

| 7,404,960 | B2 | 7/2008 | Francon |
| 2002/0137903 | A1 | 9/2002 | Ellsworth et al. |
| 2003/0114390 | A1 | 6/2003 | Washburn et al. |
| 2003/0180316 | A1 | 9/2003 | Boutriau et al. |
| 2004/0048336 | A1 | 3/2004 | Kim et al. |
| 2004/0202668 | A1 | 10/2004 | Boutriau et al. |
| 2008/0069835 | A1 | 3/2008 | Boutriau et al. |
| 2009/0214592 | A1 | 8/2009 | O'Hagan |
| 2010/0034850 | A1 | 2/2010 | DeHemptinne et al. |
| 2010/0040647 | A1 | 2/2010 | DeHemptinne et al. |
| 2010/0158951 | A1 | 6/2010 | Randolph et al. |
| 2010/0226932 | A1 | 9/2010 | Smith et al. |
| 2011/0195086 | A1 | 8/2011 | Caulfield et al. |
| 2011/0311574 | A1 | 12/2011 | Borkowski |
| 2011/0311575 | A1 | 12/2011 | Contorni |
| 2011/0311576 | A1 | 12/2011 | Contorni |

FOREIGN PATENT DOCUMENTS

| AU | 759221 | 6/2000 |
| EP | 0484621 | 5/1993 |
| EP | 1385856 | 2/2006 |
| GB | 777018 | 6/1957 |
| GB | 928807 | 6/1963 |
| GB | 759221 | 6/2000 |
| GB | 0617602.8 | 9/2006 |
| GB | 0625593.9 | 12/2006 |
| GB | 0617602.8 | 12/2007 |
| GB | 06025593.9 | 12/2007 |
| JP | 2000/504032 | 4/2000 |
| WO | 93/24148 | 9/1993 |
| WO | 96/34623 | 7/1996 |
| WO | 96/40242 | 12/1996 |
| WO | 97/00697 | 9/1997 |
| WO | WO98/00167 | 1/1998 |
| WO | 99/13906 | 3/1999 |
| WO | 199948525 | 9/1999 |
| WO | 2002/000249 | 3/2002 |
| WO | 2002/083066 | 10/2002 |
| WO | 02080965 A2 | 10/2002 |
| WO | WO 02/080965 * | 10/2002 |
| WO | WO2004/039399 | 5/2004 |
| WO | 2005089794 | 9/2005 |

(Continued)

OTHER PUBLICATIONS

Coursaget et al (Developments in biological standardization, (1986) V 65, pp. 169-175).*
Aristegui et al , Vaccine, (Aug. 2003) vol. 21, No. 25-26, pp. 3593-3600.*
Halperin et al , Human Vaccines (2005), 1(6), 245-250.*
T.M.P.T. Herremans, et al., *Induction of mucosal immunity by inactivated poliovirus vaccine is dependent on previous mucosal contact with live virus*, J. Immunol., vol. 162, pp. 5011-5018 (1999). XP002463164.
Y. Doi, et al., *Progress with inactivated poliovirus vaccines derived from the Sabin strains*, Developments in Biologicals, vol. 105, pp. 163-169 (2001). XP009040789.

(Continued)

*Primary Examiner* — Padma V Baskar
(74) *Attorney, Agent, or Firm* — Eric J. Kron

(57) ABSTRACT

The standard dose of polio vaccines contains 40 D-antigen units of inactivated poliovirus type 1 (Mahoney), 8 D-antigen units of inactivated poliovirus type 2 (MEF-1), and 32 D-antigens units of inactivated poliovirus type 3 (Saukett). The present invention teaches that reduced doses of inactivated poliovirus can maintain adequate or improved level of protection against polio.

14 Claims, 3 Drawing Sheets

(56) References Cited

FOREIGN PATENT DOCUMENTS

| WO | 2005/092877 | 10/2005 |
|---|---|---|
| WO | 2008028956 | 3/2008 |
| WO | 2008028957 | 3/2008 |
| WO | 20100046935 | 4/2010 |

OTHER PUBLICATIONS

E.M. Dragunsky, et al., *Evaluation of immunogenicity and protective properties of inactivated poliovirus vaccines: a new surrogate method for predicting vaccine efficacy*, JID, vol. 190 No. 8, pp. 1404-1412 (2004). XP009040799.
H. Bedford, et al., *Misconceptions about the new combination vaccine*, BMJ, vol. 329, pp. 411-412 (2004). XP002463165.
Bottiger, Margareta et al., (1992) Biologicals, vol. 20; pp. 267-275.
Duchene, et al., (2006), Biologicals, vol. 105; pp. 163-166.
Ellis, et al., (1999), Vaccine, vol. 17; pp. 1635-1642.
Hofman, et al., (1972), Bullentin of World Health Organization, vol. 46; pp. 735-745.
Krishnan, et al., (1983), Bullentin of World Health Organization, vol. 61/4; pp. 689-692.
Mazert, et al., (1983), Development in Biological Standardization, vol. 54; pp. 53-62.
Mmwr, et al., (1999), Combination Vaccines for Childhood Immunizations, vol. 48; pp. 1-15.
Murdin, et al., (1996), Vaccine, vol. 14/8; pp. 735-746.
Patridge, et al., (2007), Vaccine, vol. 25; pp. 1806-1813.
Pines, et al., (1999), Vaccine, vol. 17; pp. 1650-1656.
Rezapkin G et al., (2005), Biologicals, vol. 33; pp. 17-27.
Sawyer, et al., (1994), Vaccine, vol. 12/9; pp. 851-856.
Scheifele, et al., (2001), Vaccine, vol. 19; pp. 4720-4726.
Schmitt, et al., (2000), J. Pediatric, vol. 137; pp. 304-312.
Tichmann I et al., (2005), Vaccine, vol. 23; pp. 3272-3279.
Van Ramshorst, et al., (1967); Bullentin of World Health Organization, vol. 36; pp. 209-218.
Van Ramshorst et al., (1966); Immunology, vol. 11; pp. 297-231.
Van Steenis et al., (1981) Development in Biological Standard, Voi. 47; pp. 119-128.
Van Wezel, et al., (1984), Reviews of Infectious Disease vol. 6; pp. 335-340.
Yeh et al., (2001) Pediatric Infect. Dis., vol. 20/11; pp. S5 - S9.
Zepp, et al., (2004), Vaccine, vol. 22; pp. 2226-2233.
Yeh Sh et al., (2001) Pediatric Infectious Disease J., vol. 20, pp. 973-980.
Black et al., (2006), Vaccine, vol. 24, pp. 6163-6171.
Coursaget, et al., (1986), Infect. Immun, vol. 51, pp. 784-787.
Kersten, et al., (1999), Vaccine, vol. 17, pp. 2059-2066.
Dragunsky, et al., (2006) J Infect Dis., vol. 194 pp. 804-807.
Boostrix Polio Fachinformation 2004.
Scientific discussions about infarix hexa (Published on the EMEA web site) Oct. 21, 2005 proof of avalibility and date of disclosure of d4.
Scientific discussion for the Infarix Hexa product 2014.
European Pharmacopoeia Commission certificate relating to EPBRP1 (1999).
Declaration of Dr Michel Duchene 2012.
Meriste et al, ; Safety and immunogenicity of a primary course and booster dose of a combined diptheria, tetanus, acellular pertussis, hepatitis B and inactivated poliovirus vaccine, Scandinavian journal of infectious diseases, Jan. 2006; vol. 38, pp. 350-356.
Nirmal et al; Immune response of infants to fractional doses of intradermally administered inactivated poliovirus vaccine; Vaccine; 1998; No. 16 , pp. 928-931.
Carlsson et al Studies on a Hib-tetanus toxoid conjugate vaccine: effects of co-administered tetanus toxoid vaccine, of administration route and of combined administration with an inactivated polio vaccine Vaccine 2000 1895-6 468-478.
Pichichero et al Immunogenicity and Safety of a Combination Diphtheria, Tetanus Toxoid, Acellular Pertussis, Hepatitis B, and Inactivated Poliovirus Vaccine Coadministered with a 7-Valent Pneumococcal Conjugate Vaccine and a Haemophilus Influenzae Type b Conjugate Vaccine the journal of pediatrics 7/07 151 (1) 43-49 and 49e1-49e2.
Karger. s Potency testing of killed polio vaccine in rats Develop. biol. standard 1981 47 119-128.
Gold et al Safety and immunogenicity of haemophilus influenza vaccine (tetanus toxoid conjugate) administered concurrently or combined with diphteria and tetanus toxoids, pertussis vaccine and inactivated poliomyelitis vaccine to healthy infants at 2, 4 and 6 months Paediatric and infetious diseases journal May 1994 13 No. 5 348-355.
Mulholand et al the use of haemophilus influenzae type b tetanus toxoid conjugate vaccine mixed with diphtheria tetanus pertussis vaccine in gambian infants Vaccine june 1996 14 No. 9 905-909.
Revesz et a; SAR of benzoylpyridine s and benzophenones as p38a MAP kinase inhibitors with oral activity Bioorganic & Medicinal chemistry May 7, 2004 14(13) 3601-3605.
E. C bevvery rium et al Collaboeative study for the establishment of a biological . . . BRP for inactivated poliomyelitis vaccine 81-91.
Expert committee on biological standardization wld hlth org. techn. rep. ser 1963 259.
Expert committee on biological standardization wld hlth org. techn. rep. ser 1961 222.
Elwyn griffiths et al Regulation and standardization of IPV and IPV combination vaccines Biologicals 2006 34 159-161.
J Salk et al Antigen content of inactivated poliovirus vaccine for use in a one- or two- dos regimen Annals of clincal research 1982 14 204-212.
F Fuchs et al Establishment of European Pharmacopoeia BRP batch 2 for inactivated poliomyelitis vaccine for in vitro D antigen assay Pharmeuropia bio 2003 1 23-50.
D J Wood et al A Who collaborative study of immunogenicity assays of inactivated Poliovirus vaccines Biologicals 1995 23 301-311.
Robertoa a gardner et al Relative stability of pertussis vaccine preserved with merthiolatte . . . Applied and enviormental microbiology 1965 13 (4) 564.
D J Wood et al the second international standard for anti-polivirus sera type 1, 2 and 3 Biologicals 1992 20 203-211.
Edwin o davisson et al the preservation of poliomyelitis Clinical and experimental Jul. 6 1955 47 (1) 8-19.
S karger base! et al International symposium on preservatives Develop. Biol. Standard. 1973-4 24 155-165.
Jonas salk et al Control of influenza and polionyelits with killed virus vaccine Science 1977 195 834-847.
Olsen et al Chapter 7 Medical dosage calculations 9th ed 2007.
Atkinson et al Epidemiology vaccine preventable diseases 12th ed 2012 Second printing Appendix D (Vaccine administration).
Who Technical Report Series 2002 910 pp. 32-65.
Wood DJ, et al A New Who International Reference Reagent for Use in Potency Assays of Inactivated Poliomyelitis Vaccine Biologicals 1997 25 pp. 59-64.
Salk J, et al Theoretical and Practical Considerations in the Application of Killed Poliovirus Vaccine for the Control of Paralytic Poliomyelitis Dev. Biol. Stand 1981 47 pp. 181-198.
Vidor E, et al Reviews in Medical Virology the place of DTP/eIPV vaccine in routine pediatric vaccination Reviews in Medical Virology 1994 4 pp. 261-277.
Furesz J Developments in the production and quality control of poliovirus vaccines—Historical perspectives Biologicals 2006 34 87-90.
English language translation of 'Boostrix polio fachinformation' ('Summary of Product Characteristics'), cited Mar. 1, 2012 during opposition proceedings in EP2066344, the European equivalent of the present application.
Granted European equivalent of USSN12/440,054.

* cited by examiner a)

b)

VACCINE

This application is filed pursuant to 35 U.S.C. §371 as a U.S. National Phase Application of International Patent Application Serial No. PCT/EP2007/059390 filed Sep. 7, 2007, which claims priority from Great Britain Application No. 0617602.8 filed in the United Kingdom on Sep. 7, 2006, and from Great Britain Application No. 0625593.9 filed in the United Kingdom on Dec. 21, 2006, the contents of which are incorporated herein by reference.

FIELD OF THE INVENTION

The present invention relates to the field of vaccines for protecting against polio, and in particular to combination vaccines for protecting against polio, diphtheria, tetanus, and pertussis diseases.

BACKGROUND

Combination vaccines (which provide protection against multiple pathogens) are very desirable in order to minimise the number of immunisations required to confer protection against multiple pathogens, to lower administration costs, and to increase acceptance and coverage rates. The well-documented phenomenon of antigenic competition (or interference) complicates the development of multi-component vaccines. Antigenic interference refers to the observation that administering multiple antigens often results in a diminished response to certain antigens relative to the immune response observed when such antigens are administered individually.

Combination vaccines are known which can prevent *Bordetella pertussis, Clostridium tetani, Corynebacterium diphtheriae*, and optionally inactivated poliovirus (IPV), and/or Hepatitis B virus, and/or *Haemophilus* type B infection (see for instance WO 93/24148, WO97/00697 and WO2000/030678).

After many years of research the standard dose of polio vaccines accepted as effective within the vaccine community today contains 40 D antigen units of inactivated poliovirus type 1 (Mahoney), 8 D antigen units of inactivated poliovirus type 2 (MEF-1) and 32 D antigen units of inactivated poliovirus type 3 (Saukett) (e.g. Infanrix-IPV™).

The present inventors have surprisingly found that reduced doses of IPV can maintain an adequate or improved level of protection against polio. Such vaccines carry considerable advantages including the ability to provide more doses of IPV vaccines for the individuals in need thereof.

SUMMARY OF THE INVENTION

Accordingly, the present invention provides various reduced-dose IPV vaccines (which may only have IPV components or may have IPV components combined with other antigens).

Accordingly, in one aspect the present invention provides an IPV vaccine of the invention comprising inactivated poliovirus type 1 at a dose greater than 10 D-antigen units and less than 20 D-antigen units, e.g. 11, 12, 13, 14, 15, 16, 17, 18 or 19 D-antigen units.

In one embodiment, the present invention provides an IPV vaccine of the invention comprising inactivated poliovirus type 3 at a dose of 8-20 D-antigen units, e.g. 8, 9, 10, 11, 12, 13, 14, 15, 16, 17, 18, 19 or 20 D-antigen units.

In another embodiment, the present invention provides an IPV vaccine of the invention comprising inactivated poliovirus type 2 at a dose of 2-4 D-antigen units, e.g. 2, 3 or 4 D-antigen units.

In a further embodiment, the present invention provides an IPV vaccine of the invention further comprising diphtheria toxoid and/or tetanus toxoid and/or a pertussis vaccine in the form of killed whole-cell Pw vaccine or acellular pertussis antigens.

In a further aspect, the present invention provides an IPV vaccine of the invention which is a thiomersal free DTP-IPV combination vaccine comprising inactivated poliovirus type 1 at a dose between 10 and 36 D-antigen units.

In another embodiment, the present invention provides a thiomersal free DTP-IPV combination vaccine of the invention comprising inactivated poliovirus type 2 at a dose of 2-7 D-antigen units, e.g. 5, 6 or 7 D-antigen units.

In another embodiment, the present invention provides a thiomersal free DTP-IPV combination vaccine of the invention comprising inactivated poliovirus type 3 at a dose of 8-29 D-antigen units, e.g. 21, 22, 23, 24, 25, 26, 27, 28 or 29 D-antigen units.

In a further embodiment, the vaccines of the present invention may also comprise one or more antigens selected from the group consisting of: Hepatitis B surface antigen, *Haemophilus influenzae* b antigen(s), *Neisseria meningitidis* A antigen(s), *Neisseria meningitidis* C antigen(s), *Neisseria meningitidis* W antigen(s), *Neisseria meningitidis* Y antigen(s), *Neisseria meningitidis* B bleb or antigen(s), Hepatitis A antigen(s) and *Salmonella typhi* antigen(s), in particular capsular saccharide antigens from said bacteria.

Methods of making the vaccines of the invention are also provided.

DEFINITIONS

The term "vaccine" is optionally substitutable with the term "immunogenic composition" and vice versa.

"D-antigen units" (also referred to as "international units" or IU): The D antigenic form of the poliovirus induces protective neutralising antibodies. D antigen units referred to herein (for instance in the vaccines of the invention) are the measured total D antigen units of each unabsorbed bulk IPV antigen type prior to formulation of the final vaccine which are added in each human dose of formulated vaccine (typically 0.5 mL final volume). Reliable methods of measuring D-antigen units are well known in the art and are published, for instance, by the European Pharmacopoeia. For instance, D-antigen units may be measured using the ELISA test as described in Example 1 ("D-antigen quantification by ELISA") below. European Pharmacopoeia provides a test sample (European Pharmacopoeia Biological Reference Preparation—available from Ph. Eur. Secretariat, e.g. Code P 216 0000) for standardisation of such methods between manufacturers (Pharmeuropa Special Issue, Bio 96-2). Thus the D-antigen unit value is well understood in the art.

The term "dose" herein is typically one administration of the vaccine of the invention, which is typically one injection. A typical human dose is 0.5 mL. Of course various doses may be administered in a vaccine administration schedule.

The term "IPV" or a vaccine comprising these components herein is intended to mean inactivated polio virus type 1 (e.g. Mahoney, as preferably used, or Brunhilde as marketed by Statens Serum Institut under the name of DiTeKiPol), type 2 (e.g. MEF-1), or type 3 (e.g. Saukett), or a combination of either two or all three of these types. An example of a full (or standard) dose (40-8-32 D antigen units of IPV types 1, 2 and 3 respectively) IPV vaccine for the purposes of this invention could be Poliorix® (GSK Biologicals S.A.). Thus, where it is stated herein that X % of a standard dose of IPV is present in a vaccine of the invention it is meant D-antigen units equating to X % of 40, 8, and/or 32 D-antigen units of IPV types 1, 2 and/or 3 respectively (as measured in each bulk IPV antigen type) are formulated within each dose of said vaccine.

The terms "lipopolysaccharide" (LPS) and "lipooligosaccharide" (LOS) are interchangeable.

The term "saccharide" throughout this specification may indicate polysaccharide or oligosaccharide and includes both. The capsular saccharide antigen may be a full length polysaccharide or it may be extended to bacterial 'sized-saccharides' and 'oligosaccharides' (which naturally have a low number of repeat units, or which are polysaccharides reduced in size for manageability, but are still capable of inducing a protective immune response in a host) which are well known in the vaccine art (see for instance EP 497525).

The term "nucleic acid" herein can comprise single or double stranded deoxyribonucleic acid (DNA) or single or double stranded ribonucleic acid (RNA) or a mixture thereof.

The term "component(s)" from a pathogen or "component(s) affording protection to such a pathogen" within the vaccines of the invention herein is intended to mean one or more antigen(s) from that pathogen.

The terms "around" or "approximately" herein are taken to mean +10% of the stated value, but should be in keeping with the context of use.

The potency of reduced dose IPV of the formulations "Method of production 3" was examined in vivo in comparison with reference formulation (Poliorix formulation and DTPaIPVHB). RP of IPV was measured at doses 100%, 50%, 25% and 12.5% of standard IPV dose (40/8/32 D-antigen units for types 1/2/3).

Figure 2:
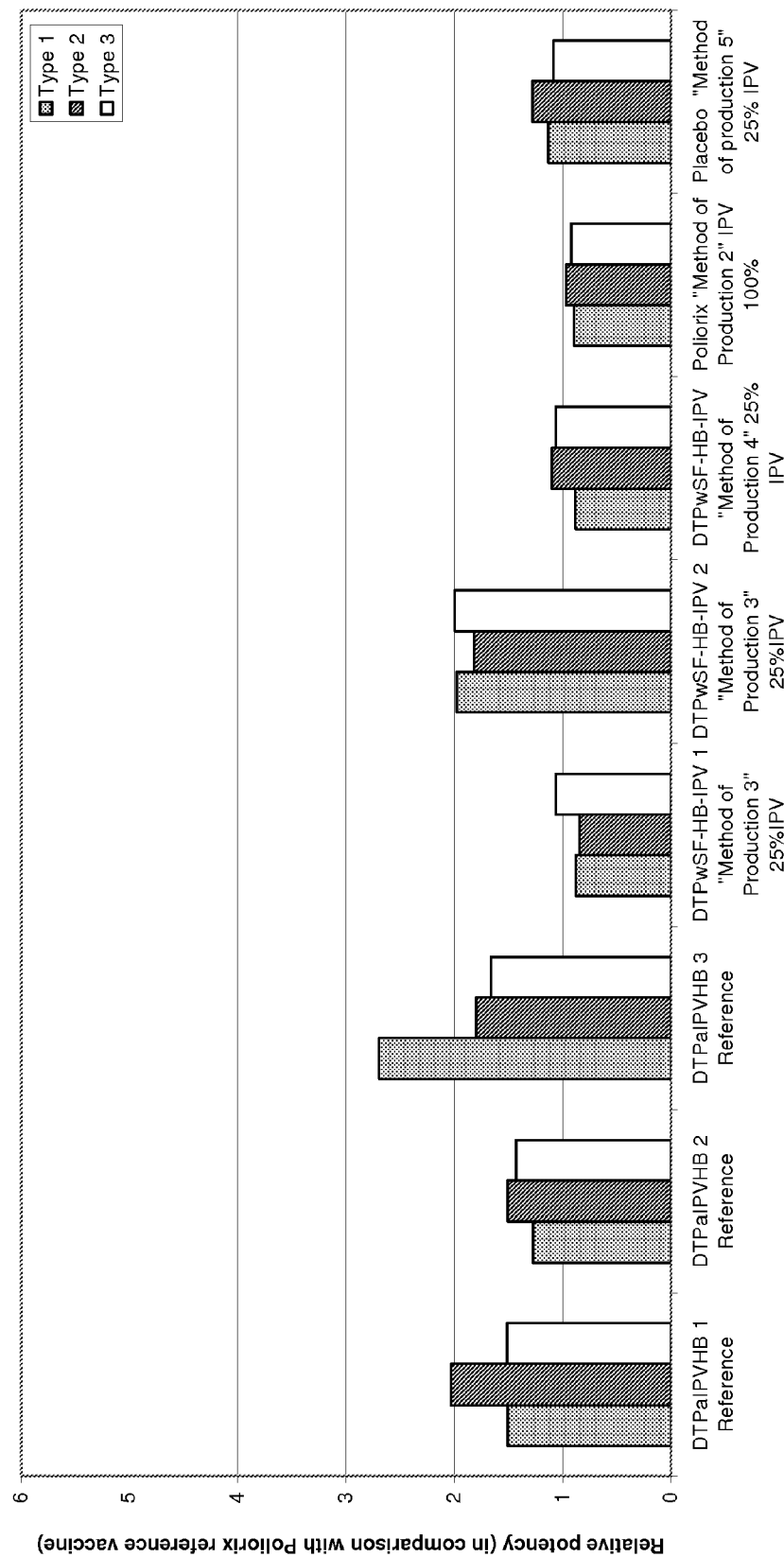

FIG. 2. Evolution of the Relative Potency (RP) of DTPw$_{SF}$-HB-IPV formulation flow-sheet.

The potency of reduced dose IPV for both formulations "Method of production 3" and "Method of production 4" was examined in vivo in comparison with reference formulations (Poliorix formulation and DTPaIPVHB). RP was measured for both "Method of production 3" and "Method of production 4" at 25% of the standard IPV dose (40/8/32 D-antigen units for types 1/2/3) in comparison to a placebo with 25% of IPV alone.

Figure 3:
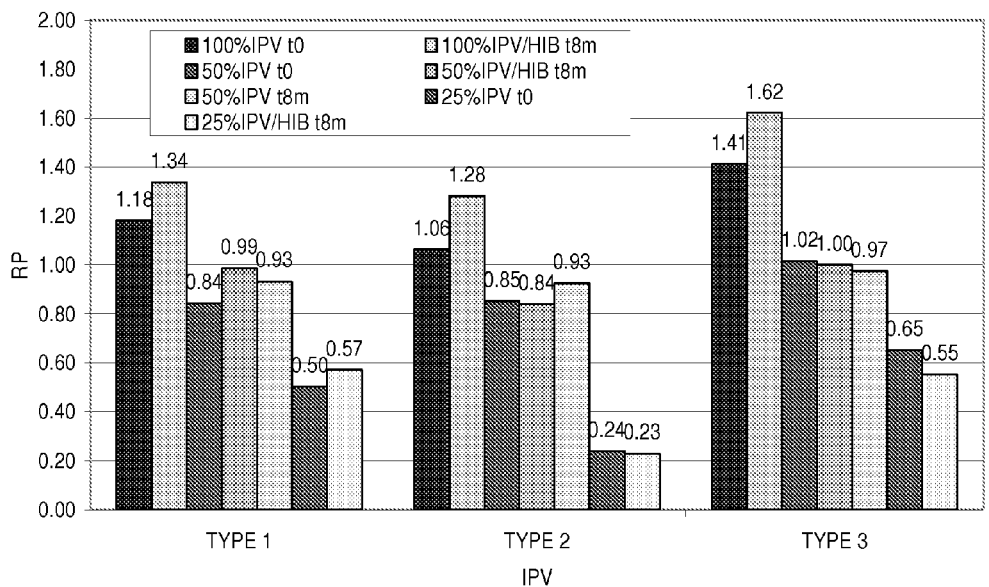
Figure 3:
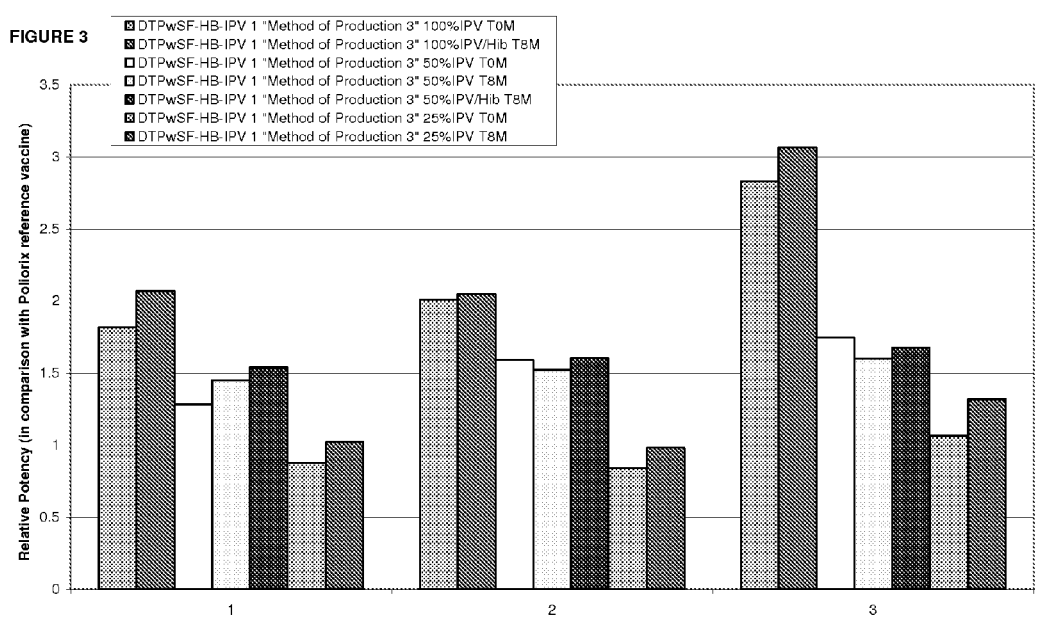

FIG. 3. Relative potency of IPV types 1, 2 and 3 at time 0 and 8 months.

Relative potency of IPV was measured [relative to DTPaH-BIPV (Pediarix) (FIG. 3a) or Poliorix (FIG. 3b)] to determine whether the Hib component has an effect on IPV potency and to evaluate the stability of IPV over time at different IPV doses.

DETAILED DESCRIPTION

The present invention provides a vaccine (e.g. a combination vaccine) comprising antigens from poliovirus (IPV) and optionally *Corynebacterium diphtheriae* (D), *Clostridium tetani* (T), *Bordetella pertussis* (P) or Hepatitis B.

The Antigens of the Invention

IPV Vaccine Components

Vaccines of the invention may be comprised of IPV type 1 or IPV type 2 or IPV type 3, or IPV types 1 and 2, or IPV types 1 and 3, or IPV types 2 and 3, or IPV types 1, 2 and 3.

Methods of preparing inactivated poliovirus (IPV) are well known in the art. In one embodiment, IPV should comprise types 1, 2 and 3 as is common in the vaccine art, and may be the Salk polio vaccine which is inactivated with formaldehyde (see for example, Sutter et al., 2000, Pediatr. Clin. North Am. 47:287; Zimmerman & Spann 1999, Am Fam Physician 59:113; Salk et al., 1954, Official Monthly Publication of the American Public Health Association 44(5):563; Hennesen, 1981, Develop. Biol. Standard 47:139; Budowsky, 1991, Adv. Virus Res. 39:255).

In one embodiment the IPV is not absorbed (e.g. before mixing with other components if present). In another embodiment, the IPV component(s) of the invention may be absorbed onto an aluminium salt such as aluminium hydroxide (e.g. before or after mixing with other components if present). In another embodiment, the IPV component(s) of the invention may be absorbed onto an aluminium salt such as aluminium phosphate. In a further embodiment the IPV component(s) may be absorbed onto a mixture of both aluminium hydroxide and aluminium phosphate. If absorbed, one or more IPV components may be absorbed separately or together as a mixture. IPV may be stabilised by a particular drying process as described in WO2004/039417.

Poliovirus may be grown in cell culture. The cell culture may be a VERO cell line or PMKC, which is a continuous cell line derived from monkey kidney. VERO cells can conveniently be cultured microcarriers. Culture of the VERO cells before and during viral infection may involve the use of bovine-derived material, such as calf serum, and this material should be obtained from sources which are free from bovine spongiform encephalitis (BSE). Culture may also involve materials such as lactalbumin hydrolysate. After growth, virions may be purified using techniques such as ultrafiltration, diafiltration, and chromatography. Prior to administration to patients, the viruses must be inactivated, and this can be achieved by treatment with formaldehyde.

Viruses may be grown, purified and inactivated individually, and then combined to give a concentrate bulk mixture for IPV vaccine use or for addition to the absorbed diphtheria and tetanus antigen and pertussis components for DTPw-IPV or DTPa-IPV comprising vaccines.

Antigens in vaccines of the invention will be present in "immunologically effective amounts" i.e. the administration of that amount to an individual, either in a single dose or as part of a series, is effective for treatment or prevention of disease. Dosage treatment may be a single dose schedule or a multiple dose schedule (e.g. including booster doses).

Standard doses of polio vaccines today tend to contain 40 D antigen units of inactivated poliovirus type 1, 8 D antigen units of inactivated poliovirus type 2 and 32 D antigen units of inactivated poliovirus type 3 (e.g. Infanrix-IPV™).

However, the present inventors have surprisingly found that reduced doses of IPV can be used to obtain a good immune response. In one embodiment, an IPV vaccine dose of the present invention may comprise between 10 and 36 D-antigen units of IPV type 1 (e.g. 11-32, 12-28, 13-24, 14-20 or 15-19 D-antigen units). In another embodiment, an IPV vaccine dose of the present invention may comprise IPV type 1 at a dose of 10-20 D-antigen units or a dose greater than 10 D-antigen units and less than 20 D-antigen units. In another embodiment, a vaccine dose of the present invention may comprise 26-49%, 30-45%, 33-40%, 35-37%, or approximately or exactly one third of a standard 40 D-antigen unit dose of IPV type 1 (equivalent to approximately 10.4-19.6, 12-18, 13.2-16, 14-14.8 or 13.3 D-antigen units). In another embodiment, an IPV vaccine dose of the present invention may comprise 11-32 D-antigen units, 12-28 D-antigen units, 13-24 D-antigen units or 14-20 D-antigen units of IPV type 1.

Alternatively, an IPV vaccine dose of the present invention may comprise 10-19.5 D-antigen units, 12-19 D-antigen units, 14-18.5 D-antigen units, or 15-17 D-antigen units; for instance around or exactly 16 D-antigen units of IPV type 1.

In a further embodiment, the vaccines of the present invention may comprise less than 4 D-antigen units, 2-4 D-antigen units (equivalent to 25-50% of a standard 8 D-antigen unit dose) or around or exactly 3 D-antigen units of IPV type 2 (equivalent to 37.5% of a standard 8 D-antigen unit dose).

In another embodiment, the vaccine of the present invention may comprise approximately or exactly one third of a standard 8 D-antigen unit dose of IPV type 2 (equivalent to approximately 2.7 D-antigen units).

In a further embodiment, the vaccines of the present invention may comprise 2-7 D-antigen units of IPV type 2. In another embodiment, an IPV vaccine dose of the present invention may comprise 3-6 D-antigen units, or 4-5 D-antigen units of IPV type 2.

Alternatively, an IPV vaccine dose of the present invention may comprise 2-4.5 D-antigen units, 2.5-4 D-antigen units or 3-3.5 D-antigen units of IPV type 2.

In a further embodiment the vaccines of the present invention may comprise 8-20 D-antigen units, more than 8 and less than 20 D-antigen units, 9-19 D-antigen units, 10-18 D-antigen units, 11-17 D-antigen units, 12-16 D-antigen units, or 13-15 D-antigen units; for instance around or exactly 14 D-antigen units of IPV type 3 (equivalent to 25-62.5%, 28.125-59.375%, 31.25-46.875% or 43.75% of a standard 32 D-antigen unit dose).

In another embodiment, the vaccine of the present invention may comprise approximately or exactly one third of a standard 32 D-antigen unit dose of IPV type 3 (equivalent to approximately 10.7 D-antigen units).

In a further embodiment, an IPV vaccine dose of the present invention may comprise 8-29 D-antigen units, 9-26 D-antigen units, 10-23 D-antigen units, 11-20 D-antigen units, 12-17 D-antigen units, or 13-14 D-antigen units of IPV type 3.

Alternatively, an IPV vaccine dose of the present invention may comprise 8-19.5 D-antigen units, 9-19 D-antigen units, 10-18.5 D-antigen units, 11-18 D-antigen units, 12-17.5 D-antigen units, 13-17 D-antigen units, or 14-16 D-antigen units; for instance around or exactly 15 D-antigen units.

DTP Vaccine Components

DTP vaccines are well known vaccines to prevent or treat diphtheria, tetanus and *B. pertussis* disease. The vaccines of the invention may comprise diphtheria, tetanus and/or pertussis component(s).

The diphtheria antigen is typically a diphtheria toxoid. The preparation of diphtheria toxoids (DT) is well documented. Any suitable diphtheria toxoid may be used. For instance, DT may be produced by purification of the toxin from a culture of *Corynebacterium diphtheriae* followed by chemical detoxification, but is alternatively made by purification of a recombinant, or genetically detoxified analogue of the toxin (for example, CRM197, or other mutants as described in U.S. Pat. Nos. 4,709,017, 5,843,711, 5,601,827, and 5,917,017). In one embodiment DT is present at an amount of 5-50, 7-30 Lf or approximately or exactly 7.5Lf or 25 Lf per 0.5 mL dose. In a further embodiment DT is present at a low dose of less than 5 Lf, or 1-4 Lf or approximately or exactly 2 Lf per 0.5 mL dose. In one embodiment, the diphtheria toxoid of the invention may be absorbed onto an aluminium salt such as aluminium hydroxide. In another embodiment, the diphtheria toxoid of the invention may be absorbed onto an aluminium salt such as aluminium phosphate. In a further embodiment the diphtheria toxoid may be absorbed onto a mixture of both aluminium hydroxide and aluminium phosphate.

The tetanus antigen of the invention is typically a tetanus toxoid. Methods of preparing tetanus toxoids (TT) are well known in the art. In one embodiment TT is produced by purification of the toxin from a culture of *Clostridium tetani* followed by chemical detoxification, but is alternatively made by purification of a recombinant, or genetically detoxified analogue of the toxin (for example, as described in EP 209281). Any suitable tetanus toxoid may be used. 'Tetanus toxoid' may encompass immunogenic fragments of the full-length protein (for instance Fragment C—see EP 478602). In one embodiment TT is present at an amount of 2.5-30 Lf, 3-20 Lf, 5-15 Lf or exactly or approximately 10 Lf per 0.5 mL dose. In one embodiment, the tetanus toxoid of the invention may be absorbed onto an aluminium salt such as aluminium hydroxide. In another embodiment, the tetanus toxoid of the invention may be absorbed onto an aluminium salt such as aluminium phosphate. In a further embodiment the tetanus toxoid may be absorbed onto a mixture of both aluminium hydroxide and aluminium phosphate.

The pertussis component of the invention may be either acellular (Pa) where purified pertussis antigens are used or whole-cell (Pw) where killed whole cell pertussis is used as the pertussis component. Pw may be inactivated by several known methods, including mercury free methods. Such methods may include heat (e.g. 55-65° C. or 56-60° C., for 5-60 minutes or for 10-30 minutes, e.g. 60° C. for 30 minutes), formaldehyde (e.g. 0.1% at 37°, 24 hours), glutaraldehyde (e.g. 0.05% at room temperature, 10 minutes), acetone-I (e.g. three treatments at room temperature) or acetone-II (e.g. three treatments at room temperature and fourth treatment at 37° C.) inactivation (see for example Gupta et al., 1987, J. Biol. Stand. 15:87; Gupta et al., 1986, Vaccine, 4:185). Methods of preparing killed, whole-cell *Bordetella pertussis* (Pw) suitable for this invention are disclosed in WO 93/24148, as are suitable formulation methods for producing DT-TT-Pw-HepB vaccines. Thiomersal has been used in the past in the preparation of killed whole-cell *Bordetella pertussis* (see below). However, in one embodiment it is not used in the formulation process of the vaccines of the present invention.

A Pw dose of 5-50 IOU, 7-40 IOU, 9-35 IOU, 11-30 IOU, 13-25 IOU, 15-21 IOU or around or exactly 20 IOU is typically used.

Acellular Pa vaccines are also well known, and may comprise 2 or more antigens from: pertussis toxoid (PT), filamentous haemagglutinin (FHA), pertactin (PRN), agglutinogens 2 & 3. In one embodiment, the Pa vaccine comprises PT, FHA and PRN. Kits or vaccines of the invention may comprise PT detoxified by a well known method of formaldehyde treatment or by means of mutations (PT derivative). Substitutions of residues within the S1 subunit of the protein have been found to result in a protein which retains its immunological and protective properties of the PT, but with reduced or no toxicity (EP 322533). The detoxifying mutations discussed in the claims of EP322533 are examples of the DT detoxified mutants of the present invention. Such mutants may be used at doses lower than 20-25 µg.

In one embodiment PT is used at an amount of 2-50 µg, 5-40 µg, 10-30 µg or exactly or approximately 25 µg per 0.5 mL dose. In another embodiment PT is used at an amount of exactly or approximately 2.5 or 8 µg per 0.5 mL dose.

In one embodiment FHA is used at an amount of 2-50 µg, 5-40 µg, 10-30 µg or exactly or approximately 25 µg per 0.5 mL dose. In another embodiment FHA is used at an amount of exactly or approximately 2.5 or 8 µg per 0.5 mL dose.

In one embodiment PRN is used at an amount of 0.5-20 µg, 0.8-15 µg, 2-10 µg or exactly or approximately 8 µg per 0.5 mL dose. In another embodiment PRN is used at an amount of exactly or around 0.8 or 2.5 µg per 0.5 mL.

In one embodiment, the pertussis component of the invention may be absorbed onto an aluminium salt such as aluminium hydroxide. In another embodiment, the pertussis component of the invention may be absorbed onto an aluminium salt such as aluminium phosphate. In a further embodiment the pertussis component may be absorbed onto a mixture of both aluminium hydroxide and aluminium phosphate. For instance in one embodiment at least PRN is absorbed onto aluminium hydroxide with PT/FHA absorbed onto aluminium hydroxide, aluminium phosphate or a mixture of both.

Further Antigens

Vaccine formulations of the invention, optionally also comprising DTP (DTPw or DTPa), can additionally comprise one or more antigens selected from the group consisting of: Hepatitis B surface antigen, *Haemophilus influenzae* b antigen(s), *Neisseria meningitidis* A antigen(s), *Neisseria meningitidis* C antigen(s), *Neisseria meningitidis* W-135 antigen(s), *Neisseria meningitidis* Y antigen(s), *Neisseria meningitidis* B bleb or purified antigen(s), Hepatitis A antigen(s), *Salmonella typhi* antigen(s) and RTS,S. Typically the capsular saccharide or LOS antigens of these pathogens may be used. Antigens will typically be present at a concentration of at least 1 µg/mL each, for instance 1-20 µg/mL, 2-15 µg/mL, 2.5-10 µg/mL, 3-8 µg/mL, or 4-6 µg/mL. In general, the concentration of any antigen will be sufficient to elicit an immune response against that antigen. It is preferred that the protective efficacy of individual antigens is not removed by combining them, although actual immunogenicity (e.g. ELISA titres) may be reduced.

The further antigen(s) may in one embodiment of the invention be absorbed onto an aluminium salt such as aluminium hydroxide. In another embodiment, the further antigens of the invention may be absorbed onto an aluminium salt such as aluminium phosphate. In a further embodiment the further antigens may be absorbed onto a mixture of both aluminium hydroxide and aluminium phosphate, or may be unabsorbed.

Where a capsular saccharide or LOS antigen is used it may be conjugated to a carrier protein comprising T helper epitopes in order to enhance immunogenicity. The invention may also comprise free "carrier proteins".

As an alternative to using protein antigens in the compositions of the invention, nucleic acid encoding the antigen may be used. Protein components of the compositions of the invention may thus be replaced by nucleic acid (for instance DNA, which may be in the form of a plasmid) that encodes the protein. Similarly, compositions of the invention may comprise proteins which mimic saccharide antigens e.g. mimotopes or anti-idiotype antibodies. These may replace individual saccharide components, or may supplement them.

Hepatitis B Antigen

The preparation of Hepatitis B surface antigen (HBsAg) is well documented. See for example, Hartford et al., 1983, Develop. Biol. Standard 54:125, Gregg et al., 1987, Biotechnology 5:479, EP0226846, EP0299108. It may be prepared as follows. One method involves purifying the antigen in particulate form from the plasma of chronic hepatitis B carriers, as large quantities of HBsAg are synthesised in the liver and released into the blood stream during an HBV infection. Another method involves expressing the protein by recombinant DNA methods. The HBsAg may be prepared by expression in the *Saccharomyces cerevisiae* yeast, pichia, insect cells (e.g. Hi5) or mammalian cells. The HBsAg may be inserted into a plasmid, and its expression from the plasmid may be controlled by a promoter such as the "GAPDH" promoter (from the glyceraldehyde-3-phosphate dehydrogenase gene). The yeast may be cultured in a synthetic medium. HBsAg can then be purified by a process involving steps such as precipitation, ion exchange chromatography, and ultrafiltration. After purification, HBsAg may be subjected to dialysis (e.g. with cysteine). The HBsAg may be used in a particulate form.

As used herein the expression "Hepatitis B surface antigen" or "HBsAg" includes any HBsAg antigen or fragment thereof displaying the antigenicity of HBV surface antigen. It will be understood that in addition to the 226 amino acid sequence of the HBsAg S antigen (see Tiollais et al., 1985, Nature 317:489 and references therein) HBsAg as herein described may, if desired, contain all or part of a pre-S sequence as described in the above references and in EP0278940. In particular, the HBsAg may comprise a polypeptide comprising an amino acid sequence comprising residues 133-145 followed by residues 175-400 of the L-protein of HBsAg relative to the open reading frame on a Hepatitis B virus of ad serotype (this polypeptide is referred to as L*; see EP0414374). HBsAg within the scope of the invention may also include the preS1-preS2-S polypeptide described in EP0198474 (Endotronics) or analogues thereof such as those described in EP0304578 (McCormick and Jones) HBsAg as herein described can also refer to mutants, for example the "escape mutant" described in WO 91/14703 or EP0511855A1, especially HBsAg wherein the amino acid substitution at position 145 is to arginine from glycine.

The HBsAg may be in particle form. The particles may comprise for example S protein alone or may be composite particles, for example L*, S) where L* is as defined above and S denotes the S-protein of HBsAg. The said particle is advantageously in the form in which it is expressed in yeast.

In one embodiment, HBsAg is the antigen used in EngerixB™ (GlaxoSmithKline Biologicals S.A.), which is further described in WO93/24148.

In one embodiment, HBsAg is present at an amount of 5-20 µg, 8-15 µg or approximately or exactly 10 µg per 0.5 mL dose.

Hepatitis B surface antigen may be absorbed onto aluminium phosphate, which may be done before mixing with the other components (described in WO93/24148). The Hepatitis B component should be substantially thiomersal free (method of preparation of HBsAg without thiomersal has been previously published in EP1307473).

*Haemophilus influenzae* b Antigen(s)

Vaccines comprising antigens from *Haemophilus influenzae* type B have been described in WO97/00697. The vaccines of the invention may use any suitable *Haemophilus influenzae* type B antigen. The antigen may be capsular saccharide (PRP) from *Haemophilus influenzae* type B conjugated to a carrier protein (Hib). The saccharide is a polymer of ribose, ribitol and phosphate. The Hib antigen may optionally be absorbed onto aluminium phosphate as described in WO97/00697, or may be unabsorbed as described in WO02/00249 or may not have undergone a specific process of adsorption.

By an antigen being 'unabsorbed onto an aluminium adjuvant salt' herein it is meant for example that an express or dedicated adsorption step for the antigen on fresh aluminium adjuvant salt is not involved in the process of formulating the composition.

Hib may be conjugated to any carrier which can provide at least one T-helper epitope (examples of which are described below), and may be tetanus toxoid, diphtheria toxoid, CRM-197 (diphtheria toxin mutant) or Protein D.

Hib may be lyophilised and may be reconstituted extemporaneously (e.g. with diluent, optionally comprising other antigenic components of the vaccines of the invention).

In one embodiment, Hib is present at an amount of 5-20 μg, 8-15 μg or approximately or exactly 10 μg saccharide per 0.5 mL dose.

In a further embodiment, Hib is present at a low dose (e.g. 1-6 μg, 2-4 μg or around or exactly 2.5 μg saccharide) as described in WO 02/00249.

*Neisseria meningitidis* Types A, C, W or Y Antigens

The vaccines of the invention may further comprise a capsular saccharide of a bacterium selected from the group consisting of *N. meningitidis* type A (MenA, optionally conjugated to a carrier protein), *N. meningitidis* type C (MenC, optionally conjugated to a carrier protein), *N. meningitidis* type W-135 (MenW, optionally conjugated to a carrier protein), and *N. meningitidis* type Y (MenY, optionally conjugated to a carrier protein).

The vaccines of the invention may comprise one or more antigens from the different strains of *N. meningitidis*, which may be used alone or in any combination of two, three or four components as detailed below:

MenA, MenC, MenW, MenY, or MenA+MenC, MenA+MenW, MenA+MenY, MenC+MenW, MenC+MenY, MenW+MenY or MenA+MenC+MenW, MenA+MenC+MenY, MenA+MenW+MenY, MenC+MenW+MenY or MenA+MenC+MenW+MenY.

In one embodiment, the *Neisseria meningitidis* component(s) of the invention may be absorbed onto an aluminium salt such as aluminium hydroxide. In another embodiment, the *Neisseria meningitidis* component(s) of the invention may be absorbed onto an aluminium salt such as aluminium phosphate. In a further embodiment the *Neisseria meningitidis* component(s) may be absorbed onto a mixture of both aluminium hydroxide and aluminium phosphate. In one embodiment the *Neisseria meningitidis* component(s) may be unabsorbed onto an adjuvant, e.g. an aluminium adjuvant salt.

*Neisseria meningitidis* Type B Bleb or Antigen(s)

The vaccines of the invention may also comprise a MenB component such as an outer membrane vesicle or bleb as described in WO01/09350, WO03/105890, WO04/014417, or WO04/014418 or a conjugated MenB capsular saccharide (or derivative thereof) antigen (e.g. see WO 96/40239) or a free or conjugated L2 or L3 or L2 and L3 meningococcal LOS (as per WO 2004/014417). In one embodiment, the MenB component(s) of the invention may be absorbed onto an aluminium salt such as aluminium hydroxide. In another embodiment, the MenB component(s) of the invention may be absorbed onto an aluminium salt such as aluminium phosphate. In a further embodiment the MenB component(s) may be absorbed onto a mixture of both aluminium hydroxide and aluminium phosphate. In one embodiment the MenB component(s) may be unabsorbed onto an adjuvant, e.g. an aluminium adjuvant salt.

*Salmonella typhi* Antigen(s)

The vaccines of the invention may further comprise the Vi saccharide from *Salmonella typhi*, which may be the registered product Typherix®, described in EP1107787, or a conjugate thereof (e.g. with a carrier protein as described herein). The conjugation process may be carried out as described in WO 2007/000343. In one embodiment, the Vi saccharide(s) of the invention may be absorbed onto an aluminium salt such as aluminium hydroxide. In another embodiment, the Vi saccharide(s) of the invention may be absorbed onto an aluminium salt such as aluminium phosphate. In a further embodiment the Vi saccharide(s) may be absorbed onto a mixture of both aluminium hydroxide and aluminium phosphate. In one embodiment the Vi saccharide(s) may be unabsorbed onto an adjuvant, e.g. an aluminium adjuvant salt.

Hepatitis A Antigen(s)

The component affording protection against Hepatitis A may be a killed attenuated Hepatitis A vaccine, for example the product known as Havrix™ (Registered Trade Mark of GlaxoSmithKline Biologicals S.A.) which is a killed attenuated vaccine derived from the HM-175 strain of Hepatitis A virus (HAV) (see "Inactivated Candidate Vaccines for Hepatitis A" by F. E. Andre et al., 1980, Prog. Med. Virol. 37:72 and the product monograph "Havrix" published by SmithKline Beecham Biologicals 1991). Flehmig et al. (1990, Prog. Med. Virol. 37:56) have reviewed the clinical aspects, virology, immunology and epidemiology of Hepatitis A and discussed approaches to the developments of vaccines against this common viral infection. As used herein the expression "HAV antigen" refers to any antigen capable of stimulating neutralising antibody to HAV in humans. In one embodiment the HAV antigen comprises inactivated attenuated virus particles, or in another embodiment it may be a HAV capsid or HAV viral protein, which may conveniently be obtained by recombinant DNA technology. In one embodiment, the Hepatitis A component of the invention may be absorbed onto an aluminium salt such as aluminium hydroxide. In another embodiment, the Hepatitis A component of the invention may be absorbed onto an aluminium salt such as aluminium phosphate. In a further embodiment the Hepatitis A component may be absorbed onto a mixture of both aluminium hydroxide and aluminium phosphate.

Malarial Antigen(s)

The vaccines of the invention may further comprise Malarial antigen(s). The Malarial antigen may be RTS,S (hybrid protein between CS and HBsAg—described in U.S. Pat. No. 6,306,625 and EP 0614465). In one embodiment, RTS,S may be used in the vaccines of the invention in place of HBsAg. Other Malarial antigens may also be used in the vaccines of the invention, including CS protein, RTS, TRAP, 16 kD protein of B 2992, AMA-1, MSP1, optionally including CpG (WO2006/029887, WO98/05355, WO01/00231).

In one embodiment, the Malarial antigen(s) of the invention may be absorbed onto an aluminium salt such as aluminium hydroxide. In another embodiment, the Malarial antigen(s) of the invention may be absorbed onto an aluminium salt such as aluminium phosphate. In a further embodiment the Malarial antigen(s) may be absorbed onto a mixture of both aluminium hydroxide and aluminium phosphate. In one embodiment the Malarial antigen is adjuvanted with an oil-in-water emulsion and/or lipid A derivative (such as MPL) and or sterol (such as cholesterol) and/or tocol (such as α-tocopherol) In another embodiment the Malaria antigen(s) may be unabsorbed onto an adjuvant, e.g. an aluminium adjuvant salt.

Conjugates

Bacterial capsular saccharide conjugates of the invention may comprise any carrier peptide, polypeptide or protein comprising at least one T-helper epitope. The carrier protein(s) used may be selected from the group consisting of: tetanus toxoid, diphtheria toxoid, CRM197, recombinant diphtheria toxin (as described in any of U.S. Pat. No. 4,709, 017, WO 93/25210, WO 95/33481, or WO 00/48638), pneumolysin (optionally chemically detoxified, or a detoxified mutant) from *S. pneumoniae* (see e.g. WO 2004/081515 and references referred to therein), OMPC from *N. meningitidis* (EP 0372501), and protein D (PD) from *H. influenzae* (EP 594610). Other carriers may include synthetic peptides (EP 0378881; EP 0427347), heat shock proteins (WO 93/17712;

WO 94/03208), pertussis proteins (WO 98/58668; EP 0471177), cytokines (WO 91/01146), lymphokines (WO 91/01146), hormones (WO 91/01146), growth factors (WO 91/01146), artificial proteins comprising multiple human CD4+ T cell epitopes from various pathogen-derived antigens (Falugi et al., 2001, Eur. J. Immunol. 31:3816), pneumococcal surface protein PspA (WO 02/091998), iron uptake proteins (WO 01/72337), toxin A or B from *C. difficile* (WO 00/61761), pneumococcal PhtD (WO 00/37105), pneumococcal PhtDE (e.g. WO 01/98334 & WO 03/054007), PhtX, etc.

Saccharides may all be on the same carrier, particularly all saccharides from a particular organism, for instance MenA, MenC, MenW and MenY saccharides may all be conjugated to TT, DT or CRM-197. However, due to the known effect of carrier suppression, it may be advantageous if in each of the compositions of the invention the saccharide antigens contained therein ('n' antigens) are conjugated to more than one carrier. Thus (n-1) of the saccharides could be carried (separately) on one type of carrier, and 1 on a different carrier, or (n-2) on one, and 2 on two different carriers, etc. For example, in a vaccine containing 4 bacterial saccharide conjugates, 1, 2 or all four could be conjugated to different carriers). Protein D, however, may be used for various (2, 3, 4 or more) saccharides in a composition without a marked carrier suppression effect. Hib may be present as a TT, DT or CRM197 conjugate, and MenA, MenC, MenY and MenW may be either TT, DT, CRM197 or PD conjugates. Vi may be present as a TT, DT or CRM197 conjugate. Protein D is a useful carrier as it provides a further antigen which can provide protection against *H. influenzae*. In one embodiment, all saccharides are conjugated to the same carrier protein.

Vi may be conjugated to a carrier protein for instance by a method using carbodiimide (e.g. EDAC) condensation chemistry (given that the Vi repeat subunit comprises carboxylic acid groups). This could be achieved either by (i) a single carbodiimide reaction between COOH of Vi and $NH_2$ of protein or (ii) a double carbodiimide reaction which can occur either between COOH of Vi and $NH_2$ of a homobifunctional linker molecule and COOH of protein and $NH_2$ of the homobifunctional linker molecule, or between COOH of Vi and $NH_2$ of the heterobifunctional linker molecule and $NH_2$ of protein and COOH of the heterobifunctional linker molecule.

Conjugation may be used in conjunction with free carrier protein(s). In one embodiment, when a given carrier protein is present in both free and conjugated form in a composition of the invention, the unconjugated form is no more than 5% of the total amount of the carrier protein in the composition as a whole, or in another embodiment is present at less than 2% by weight.

The saccharide may be linked to the carrier protein by any known method (for example, by Likhite, U.S. Pat. No. 4,372, 945 and by Armor et al., U.S. Pat. No. 4,474,757), with any suitable linker where necessary.

The saccharide will typically be activated or functionalised prior to conjugation. Activation may involve, for example, cyanylating agents such as CDAP (1-cyano-dimethylaminopyridinium tetrafluoroborate) (WO 95/08348 & WO 96/29094). The cyanilation reaction can be performed under relatively mild conditions, which avoids hydrolysis of the alkaline sensitive saccharides. This synthesis allows direct coupling to a carrier protein. Other suitable techniques use carbodiimides, hydrazides, active esters, norborane, p-nitrobenzoic acid, N-hydroxysuccinimide, S—NHS, EDC or TSTU.

Linkages via a linker group may be made using any known procedure, for example, the procedures described in U.S. Pat. Nos. 4,882,317 and 4,695,624. One type of linkage involves reductive amination of the saccharide, coupling the resulting amino group with one end of an adipic acid linker group (EP 0477508, Porro et al., 1985, Mol. Immunol. 22:907, EP 0208375), and then coupling a protein to the other end of the adipic acid linker group. Other linkers include B-propionamido (WO 00/10599), nitrophenyl-ethylamine (Gever et al., 1979, Med. Microbiol. Immunol. 165:171), haloacyl halides (U.S. Pat. No. 4,057,685), glycosidic linkages (U.S. Pat. Nos. 4,673,574; 4,761,283; 4,808,700), 6-aminocaproic acid (U.S. Pat. No. 4,459,286), ADH (U.S. Pat. No. 4,965,338), C4 to C12 moieties (U.S. Pat. No. 4,663,160), etc. As an alternative to using a linker, direct linkage can be used. Direct linkages to the protein may comprise oxidation of the saccharide followed by reductive amination with the protein, as described in, for example U.S. Pat. Nos. 4,761,283 and 4,356,170 or a direct CDAP reaction.

After conjugation, free and conjugated saccharides can be separated. There are many suitable methods for this separation, including hydrophobic chromatography, tangential ultrafiltration, diafiltration, etc (see also Lei et al., 2000, Dev Biol. (Basel). 103:259; WO 00/38711; U.S. Pat. No. 6,146, 902). In one embodiment, if a vaccine comprises a given saccharide in both free and conjugated forms, the unconjugated form is no more than 20% by weight of the total amount of that saccharide in the composition as a whole (e.g. ≤15%, ≤10%, ≤5%, ≤2%, ≤1%).

An amount of saccharide which is capable of conferring protection to a host (an effective amount) can be determined by the skilled person. In one embodiment, each dose will comprise 0.1-100 μg of saccharide, in another embodiment each dose will comprise 0.1-50 μg, in a further embodiment each dose will comprise 0.1-10 μg, in yet another embodiment each dose will comprise 1 to 5 μg.

Adjuvants

The vaccines of the invention may include a pharmaceutically acceptable excipient such as a suitable adjuvant. Suitable adjuvants include an aluminium salt such as aluminium hydroxide or aluminium phosphate, but may also be a salt of calcium, iron or zinc, or may be an insoluble suspension of acylated tyrosine, or acylated sugars, or may be cationically or anionically derivatised saccharides, polyphosphazenes, biodegradable microspheres, monophosphoryl lipid A (MPL), lipid A derivatives (e.g. of reduced toxicity), 3-O-deacylated MPL, quil A, Saponin, QS21, tocol (EP 0382271), Freund's Incomplete Adjuvant (Difco Laboratories, Detroit, Mich.), Merck Adjuvant 65 (Merck and Company, Inc., Rahway, N.J.), AS-2 (Smith-Kline Beecham, Philadelphia, Pa.), CpG oligonucleotides, bioadhesives and mucoadhesives, microparticles, liposomes, polyoxyethylene ether formulations, polyoxyethylene ester formulations, muramyl peptides or imidazoquinolone compounds (e.g. imiquamod and its homologues). Human immunomodulators suitable for use as adjuvants in the invention include cytokines such as interleukins (e.g. IL-1, IL-2, IL-4, IL-5, IL-6, IL-7, IL-12, etc), macrophage colony stimulating factor (M-CSF), tumour necrosis factor (TNF), granulocyte, macrophage colony stimulating factor (GM-CSF) may also be used as adjuvants.

In one embodiment of the invention, the adjuvant composition of the formulations induces an immune response predominantly of the TH1 type. High levels of TH1-type cytokines (e.g. IFN-γ, TNFα, IL-2 and IL-12) tend to favour the induction of cell mediated immune responses to an administered antigen. Within one embodiment, in which a response is predominantly TH1-type, the level of TH1-type cytokines will increase to a greater extent than the level of TH2-type cytokines. The levels of these cytokines may be readily assessed using standard assays. For a review of the families of cytokines, see Mosmann and Coffman, 1989, Ann. Rev. Immunol. 7:145.

Accordingly, suitable adjuvant systems which promote a predominantly TH1 response include, derivatives of lipid A (e.g. of reduced toxicity), Monophosphoryl lipid A (MPL) or a derivative thereof, particularly 3-de-O-acylated monophosphoryl lipid A (3D-MPL), and a combination of monophosphoryl lipid A, optionally 3-de-O-acylated monophosphoryl lipid A together with an aluminium salt. An enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739. A particularly potent adjuvant formulation involving QS21, 3D-MPL and tocopherol in an oil in water emulsion is described in WO 95/17210. The vaccine may additionally comprise a saponin, which may be QS21. The formulation may also comprise an oil in water emulsion and tocopherol (WO 95/17210). Unmethylated CpG containing oligonucleotides (WO 96/02555) are also preferential inducers of a TH1 response and are suitable for use in the present invention.

The vaccines of the invention may also comprise combinations of aspects of one or more of the adjuvants of the invention identified above.

Any adjuvant of the invention can be absorbed by or combined with IPV component of the invention.

When referring to aluminium hydroxide or aluminium phosphate, reference is made to all aluminium hydroxide and or aluminium phosphate adjuvants as described by Hem and White (Pharm Biotechnol. 1995; 6:249-276).

In one embodiment, aluminium phosphate may also be referred to as aluminium hydroxyphosphate. In another embodiment, aluminium phosphate has a negative charge at a pH of 7.4. Typically, the isoelectric point (pI) of aluminium phosphate is 5-7, or 6-7 or around or exactly 5. In a further embodiment, aluminium phosphate has a molar phosphate: aluminium ratio of 0.3-0.9, or 0.3-0.6, or 0.8-0.9.

In one embodiment, aluminium hydroxide has a positive charge at a pH of 7.4. Typically, the pI of aluminium hydroxide is 8-11, 9-11, 10-11 or around or exactly 11.

Typically, the total aluminium content is 200-1000 μg, 300-900 μg, 400-800 μg, 500-700 μg or around or exactly 630 μg $Al^{3+}$ per 0.5 mL dose. This may be all aluminium hydroxide or all aluminium phosphate. Alternatively $Al^{3+}$ content may be from a mixture of aluminium hydroxide and aluminium phosphate in the following ratio: 1:8-8:1, 1:4-4:1, 3:8-8:3, 1:2-2:1 or 1:1 of aluminium phosphate: aluminium hydroxide. In one embodiment a ratio of 12:1-4:1, 11:1-5:1, 10:1-6:1, 9:1-7:1 or 8:1 of aluminium phosphate: aluminium hydroxide is used.

Although most aluminium is provided by preabsorbed antigens before mixture to form a combination vaccine, some aluminium may be added in free form during formulation of the combination vaccine of the invention, e.g. before the pH adjustment step described herein. Typically, free aluminium content per 0.5 mL dose may be 0-300 μg, 50-250 μg, 75-200 μg, 100-150 μg or around or exactly 115 μg of $Al^+$. Free $Al^{3+}$ may be all $Al(OH)_3$ or all $AlPO_4$, or a mixture of $Al(OH)_3$ and AlPO4 in the following ratio (w:w $Al^{3+}:Al^{3+}$): 1:1-1:6, 1:1.1-1:5, 1:1.2-1:4, 1:1.3-1:3, 1:1.4-1:2, e.g. 23/92 or 69/46 or 6:1-1:1, 5:1-1.1:1, 4:1-1.2:1, 3:1-1.3:1, 2:1-1.4:1, e.g. 46/69 or 92/23.

Alternatively certain components of the vaccines of the invention may be not expressly absorbed onto adjuvant, in particular aluminium salts.

IPV may be unabsorbed or absorbed onto $Al(OH)_3$ or a mixture of $Al(OH)_3$ and $AlPO_4$. DT may be absorbed onto $Al(OH)_3$ or $AlPO_4$, TT may be absorbed onto $Al(OH)_3$ or $AlPO_4$, Pw may be absorbed onto or mixed with $AlPO_4$, PRN may be absorbed onto $Al(OH)_3$, FHA may be absorbed onto $Al(OH)_3$, PT may be absorbed onto $Al(OH)_3$, HB may be absorbed onto $AlPO_4$, Hib may be absorbed onto $AlPO_4$ or unabsorbed, Men ACWY may be absorbed onto $Al(OH)_3$ or $AlPO_4$ or unabsorbed, MenB component may be absorbed onto $Al(OH)_3$ or $AlPO_4$ or unabsorbed, Vi may be absorbed onto Al(OH) 3 or $AlPO_4$ or unabsorbed, HepA may be absorbed onto $Al(OH)_3$ or $AlPO_4$.

Antigens which are preabsorbed onto an aluminium salt can be preabsorbed individually prior to mixing. In another embodiment, a mix of antigens may be preabsorbed prior to mixing with further adjuvants. In one embodiment, IPV may be absorbed separately or as a mixture of IPV types 1, 2 and 3 or when mixed with absorbed D and T components.

The meaning of "absorbed antigen" is for example taken to mean greater than 20%, 30%, 40%, 50%, 60%, 70%, 80%, or 90% absorbed.

The meaning of the terms "aluminium phosphate" and "aluminium hydroxide" as used herein includes all forms of aluminium hydroxide or aluminium phosphate which are suitable for adjuvanting vaccines. For example, aluminium phosphate can be a precipitate of insoluble aluminium phosphate (amorphous, semi-crystalline or crystalline), which can be optionally but not exclusively prepared by mixing soluble aluminium salts and phosphoric acid salts. "Aluminium hydroxide" can be a precipitate of insoluble (amorphous, semi-crystalline or crystalline) aluminium hydroxide, which can be optionally but not exclusively prepared by neutralising a solution of aluminium salts. Particularly suitable are the various forms of aluminium hydroxide and aluminium phosphate gels available from commercial sources for example, Alhydrogel (aluminium hydroxide, 3% suspension in water) and Adjuphos (aluminium phosphate, 2% suspension in saline) supplied by Brenntag Biosector (Denmark).

Non-Immunological Components of Vaccines of the Invention

Vaccines of the invention will typically, in addition to the antigenic and adjuvant components mentioned above, comprise one or more "pharmaceutically acceptable carriers or excipients", which include any excipient that does not itself induce the production of antibodies harmful to the individual receiving the composition. Suitable excipients are typically large, slowly metabolised macromolecules such as proteins, saccharides, polylactic acids, polyglycolic acids, polymeric amino acids, amino acid copolymers, sucrose (Paoletti et al., 2001, Vaccine, 19:2118), trehalose (WO 00/56365), lactose and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate buffered physiologic saline is a typical carrier. A thorough discussion of pharmaceutically acceptable excipients is available in reference Gennaro, 2000, Remington: The Science and Practice of Pharmacy, $20^{th}$ edition, ISBN:0683306472.

Compositions of the invention may be lyophilised or in aqueous form, i.e. solutions or suspensions. Liquid formulations of this type allow the compositions to be administered direct from their packaged form, without the need for reconstitution in an aqueous medium, and are thus ideal for injection. Compositions may be presented in vials, or they may be presented in ready filled syringes. The syringes may be supplied with or without needles. A syringe will include a single dose of the composition, whereas a vial may include a single dose or multiple doses (e.g. 2 doses). In one embodiment the dose is for human. In a further embodiment the dose is for an adult, adolescent, toddler, infant or less than one year old human and may be administered by injection.

Liquid vaccines of the invention are also suitable for reconstituting other vaccines from a lyophilised form. Where a vaccine is to be used for such extemporaneous reconstitution, the invention provides a kit, which may comprise two vials, or may comprise one ready-filled syringe and one vial, with the contents of the syringe being used to reconstitute the contents of the vial prior to injection.

Vaccines of the invention may be packaged in unit dose form or in multiple dose form (e.g. 2 doses). For multiple dose forms, vials are preferred to pre-filled syringes. Effective dosage volumes can be routinely established, but a typical human dose of the composition for injection has a volume of 0.5 mL.

In one embodiment, vaccines of the invention have a pH of between 6.0 and 8.0, in another embodiment vaccines of the invention have a pH of between 6.3 and 6.9, e.g. 6.6±0.2. Vaccines may be buffered at this pH. Stable pH may be maintained by the use of a buffer. If a composition comprises an aluminium hydroxide salt, a histidine buffer may be used (WO03/009869). The composition should be sterile and/or pyrogen free.

Compositions of the invention may be isotonic with respect to humans.

Vaccines of the invention may include an antimicrobial, particularly when packaged in a multiple dose format. Thiomersal should be avoided as this leads to loss of potency of the IPV component. Other antimicrobials may be used, such as 2-phenoxyethanol or parabens (methyl, ethyl, propyl parabens). Any preservative is preferably present at low levels. Preservative may be added exogenously and/or may be a component of the bulk antigens which are mixed to form the composition (e.g. present as a preservative in pertussis antigens).

In one embodiment, vaccines of the invention are thiomersal free or substantially thiomersal free. By "thiomersal free" or "substantially thiomersal free" it is meant that there is not enough thiomersal present in the final formulation to negatively impact the potency of the IPV component. For instance, if thiomersal is used during the Pw or Hepatitis B surface antigen purification process it should be substantially removed prior to mixture with IPV. Thiomersal content in the final vaccine should be less than 0.025 µg/µg protein, 0.024 µg/µg protein, 0.01 µg/µg protein or 0.001 µg/µg protein, for instance 0 µg/µg protein. In one embodiment, thiomersal is not added nor used in the purification of any component. See for instance EP1307473 for Hepatitis B and see above for Pw processes where killing is achieved not in the presence of thiomersal.

Vaccines of the invention may comprise detergent e.g. a Tween (polysorbate), such as Tween 80. Detergents are generally present at low levels e.g. <0.01%.

Vaccines of the invention may include sodium salts (e.g. sodium chloride) to give tonicity. The composition may comprise sodium chloride. In one embodiment, the concentration of sodium chloride in the composition of the invention is in the range of 0.1 to 100 mg/mL (e.g. 1-50 mg/mL, 2-20 mg/mL, 5-15 mg/mL) and in a further embodiment the concentration of sodium chloride is 10±2 mg/mL NaCl e.g. about 9 mg/mL.

Vaccines of the invention will generally include a buffer. A phosphate or histidine buffer is typical.

Vaccines of the invention may include free phosphate ions in solution (e.g. by the use of a phosphate buffer) in order to favour non-adsorption of antigens. The concentration of free phosphate ions in the composition of the invention is in one embodiment between 0.1 and 10.0 mM, or in another embodiment between 1 and 5 mM, or in a further embodiment about 2.5 mM.

Properties of the Vaccines of the Invention

In one embodiment the vaccines of the invention are formulated as a vaccine for in vivo administration to the host in such a way that the individual components of the composition are formulated such that the immunogenicity of individual components is not substantially impaired by other individual components of the composition. By not substantially impaired, it is meant that upon immunisation, an antibody titre against each component is obtained which is more than 60%, 70%, 80% or 90%, or 95-100% of the titre obtained when the antigen is administered in isolation. Thus, in preferred embodiments, no (significantly) detrimental effect occurs to the further components (in terms of protective efficacy) in the combination as compared to their administration in isolation.

Vaccine Formulations

In one embodiment, the vaccines of the invention are formulated as a vaccine for in vivo administration to the host, such that they confer an antibody titre superior to the criterion for seroprotection for each antigenic component for an acceptable percentage of human subjects. This is an important test in the assessment of a vaccine's efficacy throughout the population. Antigens with an associated antibody titre above which a host is considered to be seroconverted against the antigen are well known, and such titres are published by organisations such as WHO. In one embodiment, more than 80% of a statistically significant sample of subjects is seroconverted, in another embodiment more than 90% of a statistically significant sample of subjects is seroconverted, in a further embodiment more than 93% of a statistically significant sample of subjects is seroconverted and in yet another embodiment 96-100% of a statistically significant sample of subjects is seroconverted.

The amount of antigen in each vaccine dose is selected as an amount which induces an immunoprotective response without significant, adverse side effects in typical vaccines. Such amount will vary depending on which specific immunogens are employed. Generally it is expected that each dose will comprise 1-1000 µg of total immunogen, or 1-100 µg, or 1-40 µg, or 1-5 µg. An optimal amount for a particular vaccine can be ascertained by studies involving observation of antibody titres and other responses in subjects. A primary vaccination course may include 2-3 doses of vaccine, given one to two months apart, e.g. following the WHO recommendations for DTP immunisation (i.e. in first year of life). Booster doses may follow in the second and/or subsequent year(s) of life.

Polio Potency as Measured by Seroneutralisation Test on Rats

For the purposes of the invention, the assay for the IPV quantitative evaluation of the vaccine potency of the IPV containing vaccines of the invention should be carried out using a single dose of vaccine and should be done by determining the ratio of test vaccine geometric mean titre (GMT) to reference vaccine GMT and is reported as the relative response (RR) or relative potency (RP). Reference GMT may be the GMT obtained with any IPV vaccine comprising 40-8-32 D-antigen units of IPV types 1-2-3 respectively, and may be the GMT obtained with the known vaccine Poliorix®. Typically, the RP test is carried out by as follows:

The potency of poliovirus Types 1, 2 and 3 is determined on rats by seroneutratisation:

Groups of 10 healthy rats (Sprague-Dawley (OFA) or any beforehand validated strain) are inoculated intramuscularly with dilutions ($1/1.25$; $1/3.125$; $1/7.81$) of the test samples or reference material in phosphate buffer saline. If necessary, the dilution range may be extended to 4 dilutions by inoculating undiluted vaccine and the three previous mentioned dilutions. Ten rats inoculated with the diluent are used as negative controls. Rats are observed once a week to detect any abnormal reaction. 20 to 22 days after the inoculation, each animal is deeply anesthetized, and bled and the serum is collected to be analysed by seroneutralisation test.

For the seroneutralisation test, sera are inactivated by incubation at 56° C. for 30 minutes in a water bath. Three dilution series of the sera, one for each polio type, are prepared in microplates using the appropriate dilution medium. Plates are stored at +4° C.

For the three polio virus types, a predetermined amount of virus (30-300 $CCID_{50}$) is added to the sera dilutions. The three virus suspensions are diluted taking into account their respective titers. The final dilution is called 'working dilution'. Each working dilution is added to the corresponding microplates. Plates are then sealed and incubated at 37° C.±1° C. for 16 hours. Hep-2 cells are then added and microplates are incubated at 37° C.±1° C. for 7 days. The cytopathogenic effect (CPE) of the virus is read using an inverted microscope after Coomassie blue coloration. The presence of anti-poliomyelitis antibodies inhibits the growth of the virus and the appearance of the corresponding CPE. The anti-polio virus titers (type 1, 2 and 3) correspond to the reciprocal of the last dilution without any CPE. In each group, animals with neutralising antibodies are recorded and the antibodies titer of each serum sample is determined for the different type of poliovirus. The neutralizing antibody titer is expressed as the $\log_2$ of the inverse of the highest dilution of the serum sample that totally inhibits the cytopathic effect of poliovirus on Hep-2 cells.

The geometric mean titer per dilution (GMT) and per virus type is also determined for each group of rats.

Packaging of Vaccines of the Invention

Vaccines of the invention can be packaged in various types of container e.g. in vials, in syringes, etc. A multidose vial will typically comprise a re-sealable plastic port through which a sterile needle can be inserted to remove a dose of vaccine, which reseals once the needle has been removed.

The vaccine may be supplied in various containers (e.g. 2 or 3). The contents of the containers may be mixed extemporaneously before administering to a host in a single injection or may be administered concomitantly at different sites. The dose of the vaccine or each vaccine if a kit is administered concomitantly (in two or more containers) will typically be 0.5 mL.

In one embodiment of this aspect of the invention there is provided a kit comprising two multi-valent vaccines for conferring protection in a host against disease caused by poliovirus, *Bordetella pertussis, Clostridium tetani, Corynebacterium diphtheriae* and optionally one or more of Hepatitis B, *Haemophilus influenza* type B, *Neisseria meningitidis* type A, *Neisseria meningitidis* type C, *Neisseria meningitidis* type W, *Neisseria meningitidis* type Y, *Neisseria meningitidis* type B, *Salmonella typhi*, Hepatitis A or Malaria.

The kit comprises a first container comprising:

(1) (a) Inactivated polio virus (IPV) of the invention, (b) diphtheria toxoid (DT or D) (see above), (c) tetanus toxoid (TT or T) (see above), (d) killed whole-cell *Bordetella pertussis* (Pw) or 2 or more acellular pertussis components (Pa) (see above), (e) optionally Hepatitis B surface antigen (HepB or HB) (see above), (f) optionally a conjugate of a carrier protein and the capsular saccharide of *H. influenzae* type B (Hib) (see above), (g) optionally either or both conjugates of a carrier protein and a capsular saccharide of a *N. meningitidis* type A (MenA) or *N. meningitidis* type C (MenC) (see above), and a second container comprising:

(2A) (a) conjugates of a carrier protein and a capsular saccharide *N. meningitidis* type A (MenA), *N. meningitidis* type C (MenC), *N. meningitidis* type W (MenW) and/or *N. meningitidis* type Y (MenY) (see above for various Men saccharide combinations of the invention), and (b) optionally a conjugate of a carrier protein and the capsular saccharide of *H. influenzae* type B (Hib); or (2B) (a) a conjugate of a carrier protein and the capsular saccharide of *H. influenzae* type B (Hib), and (b) optionally a conjugate of a carrier protein and Vi saccharide of *Salmonella typhi*

The kit may optionally comprise a third container comprising:

(3) (a) optionally Hepatitis B surface antigen (b) optionally a conjugate of a carrier protein and Vi saccharide of *Salmonella typhi*

The containers may in either case additionally comprise HepA antigen(s) and/or MenB antigen(s) and/or RTS,S and/or *Streptococcus pneumonia* antigen(s).

In either case, the same antigen should not be present in both containers.

In one embodiment the first container has in addition to components a), b), c), d) also e), f), g), e)+f), e)+g), f)+g) or e)+f)+g).

In one embodiment the vaccine of the first container may be liquid and the vaccine of the second container may be either liquid or lyophilised (e.g. in the presence of a known stabilising excipient such as sucrose or trehalose).

The containers of the kit can be packaged separately or, optionally, packed together. In one embodiment, the kit is provided with a list of instructions for administration of the vaccines in the two or more containers.

In one embodiment, where a container in a kit contains a certain saccharide conjugate, the same conjugate is not present in the other containers of the kit.

The inventors believe that a kit provided in the above way may advantageously present the various antigens to a host's immune system in an optimal manner. The kit may provide a medical practitioner with an optimal method of immunising a host with one or more of the following advantages: protective efficacy for all antigens, minimal reactogenicity, minimal carrier suppression interference, minimal adjuvant/antigen interference, or minimal antigen/antigen interference. In such a way, these goals may be achieved with the minimum number (two) administrations, optionally occurring at the same visit to the practitioner.

In one embodiment the vaccines of the first and second containers are administered concomitantly at different sites (as described below under "administration of vaccines of the invention), and in an alternative embodiment the inventors envision that the contents of the first and second containers may be mixed (optionally extemporaneously) before administration as a single vaccine.

Preparing Vaccines of the Invention The present invention also provides a method for producing a vaccine formulation comprising the step of mixing the components of the vaccine together with a pharmaceutically acceptable excipient.

In one embodiment of the present invention there is provided a vaccine as herein described for use in a medicament for the treatment or prevention of diseases caused by infection by poliovirus and optionally *Bordetella pertussis, Clostridium tetani, Corynebacterium diphtheriae*, Hepatitis B virus, *Haemophilus influenzae, Neisseria meningitidis* type A, *Neisseria meningitidis* type C, *Neisseria meningitidis* type W, *Neisseria meningitidis* type Y, *Salmonella typhi* or Hepatitis A.

In another embodiment of the invention there is provided a use of the vaccines of the invention in the manufacture of a medicament for the treatment or prevention of diseases caused by infection by poliovirus and optionally *Bordetella pertussis, Clostridium tetani, Corynebacterium diphtheriae*, Hepatitis B virus, *Haemophilus influenzae, Neisseria meningitidis* type A, *Neisseria meningitidis* type C, *Neisseria meningitidis* type W, *Neisseria meningitidis* type Y, *Salmonella typhi* or Hepatitis A.

Additionally, a method of immunising a human host against disease caused by poliovirus and optionally *Bordetella pertussis, Clostridium tetani, Corynebacterium diphtheriae*, Hepatitis B virus, *Haemophilus influenzae, Neisseria meningitidis* type A, *Neisseria meningitidis* type C, *Neisseria meningitidis* type W, *Neisseria meningitidis* type Y, *Salmonella typhi* or Hepatitis A, which method comprises administering to the host an immunoprotective dose of the vaccine of the invention is also provided.

The amount of antigen in each vaccine dose is selected as an amount which induces an immunoprotective response without significant, adverse side effects in typical vaccines. Such amount will vary depending upon which specific immunogen is employed and how it is presented. In one embodiment each dose will comprise 0.1-100 µg of saccharide, in another embodiment each dose will comprise 0.1-50 µg, in a further embodiment each dose will comprise 0.1-10 µg, in yet another embodiment each dose will comprise 1 to 5 µg saccharide.

In one embodiment, the content of protein antigens in the vaccine will be in the range 1-100 µg, in another embodiment the content of the protein antigens in the vaccines will be in the range 5-50 µg, in a further embodiment the content of the protein antigens in the vaccines will be in the range 5-25 µg.

Vaccine preparation is generally described in Vaccine Design ["The subunit and adjuvant approach" (eds Powell M. F. & Newman M. J.) (1995) Plenum Press New York]. Encapsulation within liposomes is described by Fullerton, U.S. Pat. No. 4,235,877. Conjugation of proteins to macromolecules is disclosed, for example by Likhite, U.S. Pat. No. 4,372,945 and by Armor et al., U.S. Pat. No. 4,474,757. Use of Quil A is disclosed by Dalsgaard et al., 1977, Acta Vet Scand. 18:349. 3D-MPL is available from Ribi immunochem, USA and is disclosed in British Patent Application No. 2220211 and U.S. Pat. No. 4,912,094. QS21 is disclosed in U.S. Pat. No. 5,057,540.

In a further embodiment of the invention there is provided a multi-valent vaccine comprising inactivated poliovirus (IPV) of the invention and optionally killed whole-cell *Bordetella pertussis* (Pw), tetanus toxoid (TT), diphtheria toxoid (DT), a conjugate of a carrier protein and the capsular saccharide of *H. influenzae* type B (Hib—optionally conjugated to TT, DT or CRM197), wherein the amount of conjugate per 0.5 mL dose of bulk vaccine is 1-8 µg, and the immunogenicity of the conjugate is equivalent or improved over such compositions comprising larger amounts of conjugate. Optionally, Hepatitis B surface antigen may also be included.

In one embodiment the amount of conjugate per 0.5 mL dose of bulk vaccine is less than 10 µg (of saccharide in the conjugate), in another embodiment the amount of conjugate is 1-7, in another embodiment the amount of conjugate is 2-6 µg, or in a further embodiment about 2.5, 3, 4 or 5 µg.

It will be appreciated that certain components, for example DTPw components, can be combined separately before adding the absorbed HBsAg or other components.

A method of making vaccines of the invention is also provided comprising the step of mixing IPV type 1, IPV type 2 and/or IPV type 3 with a pharmaceutically acceptable excipient. A typical process for preparing bulk vaccine of the invention with further antigens will add the IPV components to a mixture of the D and T components, i.e. the DT components are mixed with the IPV components. This order of mixing allows the ionic strength and/or pH of the composition to be adjusted (e.g. pH<7) prior to the addition of the Pa or Pw components. Typically, HB pre-absorbed onto $AlPO_4$ is added first if included in the composition, followed by the addition of DT pre-absorbed onto $Al(OH)_3$ or $AlPO_4$, followed by the addition of TT pre-absorbed onto $Al(OH)_3$ or $AlPO_4$, followed by the addition of IPV optionally pre-absorbed onto $Al(OH)_3$, prior to pH adjustment to e.g. pH5.9-7.2, or pH6-7, or pH6.2-6.8, or pH6.4-6.6, and then the addition of Pw pre-absorbed onto $AlPO_4$. Optionally, Hib, Vi, MenA, MenC, MenW, MenY, MenB and/or HepA antigens may be added at any point in this process. In one embodiment, Hib, Vi, MenA, MenC, MenW, MenY, MenB and/or HepA antigens are added prior to pH adjustment. In one embodiment one or more antigens of the invention are absorbed onto aluminium phosphate or aluminium hydroxide or a mixture of both. In another embodiment the antigens of the invention are mixed with a pharmaceutically acceptable excipient and/or adjuvant(s).

In one embodiment, the vaccine composition of the invention may be prepared in the following order: preabsorbed HBsAg is added, followed by preabsorbed Diphtheria toxoid, followed by preabsorbed tetanus toxoid and IPV, the pH is then adjusted to approximately 6.5 prior to adding preabsorbed Pw.

In another embodiment, the vaccine composition of the invention may be prepared in the following order: preabsorbed tetanus toxoid is added, followed by IPV, followed by preabsorbed HBsAg, followed by preabsorbed Diphtheria toxoid, the pH is then adjusted to approximately 6.5 prior to adding preabsorbed Pw.

In general, the combined vaccine compositions according to any aspect of the invention can be prepared as follows: The IPV, DTPw, HepB, MenA, MenC, MenW, MenY, MenB, Vi, Hepatitis A or other components are pre-absorbed onto a suitable adjuvant, especially aluminium hydroxide or aluminium phosphate or a mixture of both. After allowing time for complete and stable adsorption of the respective components, the different components are combined under appropriate conditions. The Hib, Vi, MenA, MenC, MenW and/or MenY conjugate(s) may or may not be absorbed onto aluminium adjuvant salt before being mixed with the DTPw vaccine.

In one embodiment, vaccines of the invention are prepared at between 15° C. and 30° C. (e.g. between 19° C. and 27° C., or at 23±4° C.).

Administration of Vaccines of the Invention

The invention provides a method for raising an immune response in a mammal, comprising the step of administering an effective amount of a vaccine of the invention. The vaccines can be administered prophylactically (i.e. to prevent infection). The immune response is preferably protective and preferably involves antibodies. The method may raise a booster response.

Following an initial vaccination, subjects may receive one or several booster (subsequent) immunisations adequately spaced. Dosing treatment can be a single dose schedule or a multiple dose schedule. Multiple doses may be used in a primary immunisation schedule and/or in a booster immunisation schedule. A primary dose schedule, which may be in the first year of life, may be followed by a booster dose schedule. Suitable timing between priming doses (e.g. between 4-16 weeks), and between priming and boosting can be routinely determined.

In one embodiment, the mammal is a human. Where the vaccine is for prophylactic use, the human is preferably a child (e.g. a toddler of infant) or a teenager; where the vaccine is for therapeutic use, the human is preferably an adult. A vaccine intended for children may also be administered to adults e.g. to assess safety, dosage, immunogenicity, etc.

The vaccine preparations of the present invention may be used to protect or treat a mammal susceptible to infection, by means of administering said vaccine directly to a patient. Direct delivery may be accomplished by parenteral administration (intramuscularly, intraperitoneally, intradermally, subcutaneously, intravenously, or to the interstitial space of a tissue); or by rectal, oral, vaginal, topical, transdermal, intranasal, ocular, aural, pulmonary or other mucosal administration. In one embodiment, administration is by intramuscular injection to the thigh or the upper arm. Injection may be via a needle (e.g. a hypodermic needle), but needle free injection may alternatively be used. A typical intramuscular dose is 0.5 mL.

Bacterial infections affect various areas of the body and so the compositions of the invention may be prepared in various forms. For example, the compositions may be prepared as injectables, either as liquid solutions or suspensions. The composition may be prepared for pulmonary administration e.g. as an inhaler, using a fine powder or spray. The composition may be prepared as a suppository or pessary. The composition may be prepared for nasal, aural or ocular administration e.g. as spray, drops, gel or powder (see e.g. Almeida & Alpar, 1996, J Drug Targeting, 3:455; Bergquist et al., 1998, APMIS, 106:800). Successful intranasal administration of DTP vaccines has been reported (Ryan et al., 1999, Infect. Immun., 67:6270; Nagai et al., 2001, Vaccine, 19:4824).

In one embodiment the vaccines of the first and second (and third where applicable) containers are administered concomitantly at different sites, and in an alternative embodiment the inventors envison that the contents of the first and second containers may be mixed (optionally extemporaneously) before administration as a single vaccine.

The invention may be used to elicit systemic and/or mucosal immunity.

One way of checking the efficacy of therapeutic treatment involves monitoring bacterial infection after administration of the composition of the invention. One way of checking efficacy of prophylactic treatment involves monitoring immune responses against the antigens after administration of the composition. Immunogenicity of compositions of the invention can be determined by administering them to test subjects (e.g. children 12-16 months age, or animal models—WO 01/30390) and then determining standard immunological parameters. These immune responses will generally be determined around 4 weeks after administration of the composition, and compared to values determined before administration of the composition. Rather than assessing actual protective efficacy in patients, standard animal and in vitro models and correlates of protection for assessing the efficacy of DTP vaccines are well known.

The terms "comprising", "comprise" and "comprises" herein are intended by the inventors to be optionally substitutable with the terms "consisting of", "consist of" and "consists of", respectively, in every instance. This does not change the normal meaning of these terms, and is only intended to provide basis for the substitution, not to make them equivalent in meaning.

All cited references and publications are incorporated by reference herein.

EXAMPLES

Examples are provided solely for the purposes of illustration and are not intended to limit the scope of the invention.

Example 1

Tests on Low Dose IPV Formulations

For all the formulations of the example 1, the antigens are absorbed by addition of aluminium salt prior to formulation except IPV which is added without adsorption.

The tables below present the adsorption method for D, T, Pw and HBsAg.

TABLE 1

Method of productions for Diphtheria toxoid adsorption.

$AlPO_4$
|
D (7.5 Lf/0.075 mg $Al^{3+}$)
|
Stirring 15 up to 20 min. at room t°
|
Adjust pH at pH 5.1 +/- 0.1
|
Stirring 15 up to 20 min. at room t°
|
Check pH 5.1 +/- 0.1
|
Stirring 15 up to 45 min. at room t°
|
Maturation 7 days +/- 8 Hr at 37° C. +/- 1° C. without stirring (glass vessel) with stirring (stainless steel vessel)
|
Stirring 15 up to 45 min. at room t°
|
Adjust pH at pH 6.1 +/- 0.1
|
Stirring 15 up to 20 min. at room t°
|
Check pH 6.1 +/- 0.1
|
Store minimum 7 days at +2/+8° C. before formulation FINAL COMPOSITION per dose

| | |
|---|---|
| Diphtheria | 7.5 Lf (+/−420 Lf/ml) |
| $Al^{3+}$ | 0.075 mg |
| NaCl | 150 mM |
| pH | 6.1 +/− 0.1 |
| Volume | approximately 18 μl |

TABLE 2

Method of production for Tetanus toxoid adsorption.

$Al(OH)_3$
SUPERFOS type
|
T (3.25 Lf/0.070 mg mg $Al^{3+}$)
|
Stirring 15 min. up to 20 min. at R.T.
|
Adjust at pH 6.1 +/- 0.1
|
Stirring 15 min. up to 20 min. at R.T.
|
Check pH 6.1 +/- 0.1
|
Stirring 16 hr. up to 24 hr. at R.T.
|
NaCl 1500 mM. (ad. 150 mM)
|
Stirring 15 min. up to 45 min. at R.T.
|
Adjust at pH 6.1 +/- 0.1
|
Stirring 15 min. up to 20 min. at R.T.
|
Check pH 6.1 +/- 0.1
|
Storage minimum 14 days at +2° C./+8° C.° before formulation.

FINAL COMPOSITION per dose

| | |
|---|---|
| Tetanus | 3.25 Lf (+/−360 Lf/ml) |
| $Al^{3+}$ | 0.070 mg |
| NaCl | 150 mM |
| pH | 6.1 +/- 0.1 |
| Volume | approximately 9 μl |

TABLE 3

Method of productions for Pw adorption $AlPO_4$
0.17 mg $Al^{3+}$/d
(Brenntag)
|
Adjust pH at pH 6.5 +/- 0.1
|
Stirring 15 min. up to 20 min. at room t°
|
Check pH 6.5 +/- 0.1
|
Pw
20IOU/d
|
Stirring 15 min. up to 45 min. at Room t°
|
Measure pH
|
Storage at +2° C.-+8° C.

FINAL COMPOSITION per dose

| Antigens | | Adjuvant | [$Al^{3+}$] (mg) |
|---|---|---|---|
| Pw | 20 OU | $AlPO4$ | 0.170 mg |
| $Al^{3+}$ | 0.170 mg | $AlPO4$ | |
| NaCl | 150 mM | | |
| pH | 6.8 | | |
| Volume | approximately 65 μl | | |

TABLE 4

Method of productions for HBsAg adsorption

HBsAg
10 µg
|
$Al^{3+}$ 0.20 mg
$AlPO_4$
|
Stirring 15 min. up to 30 min. at room t°
|
Adjust pH at pH 5.3 +/- 0.1
|
Stirring 15 min. up to 30 min. at room t°
|
Check pH at pH 5.3 +/- 0.1
|
Stirring 20 Hr +/- 4 Hr at room t° (adsorption)
|
Adjust pH at pH 6.1 +/- 0.1
|
Stirring 15 min. up to 30 min. at room t°
|
Check pH at pH 6.1 +/- 0.1
|
Store 14 days at room t° (maturation)
|
Storage 2° C.-8° C.

FINAL COMPOSITION per dose

| Antigens | | Adjuvant | $[Al^{3+}]$ (mg) |
|---|---|---|---|
| HBsAg | 10 µg | $AlPO_4$ | 0.200 mg |
| $Al^{3+}$ | 0.200 mg | $AlPO_4$ | |
| NaCl | 150 mM | | |
| pH | 6.1 +/- 0.1 | | |
| Volume | approximately 50 µl | | |

Several different formulations were tested:
A combination of Diptheria toxoid, Tetanus toxoid, Pertussis whole cell and Hepatitis B surface antigen: DTPw$_{SF}$-HB as a reference (DTPw$_{SF}$ means that it is a thiomersal free formulation), formulated with the production method 1 (table 5).
GlaxoSmithKline Biologicals S.A. product Poliorix® (IPV stand-alone not absorbed) as unabsorbed reference at the standard dose, formulated with the production method 2 (table 5).
A combination of Diphtheria toxoid, Tetanus toxoid, Pertussis whole cell, Hepatitis B surface antigen and Inactivated polio virus: DTPw$_{SF}$-HB-IPV with addition of the IPV before Pw, formulated with the production method 3 (table 5).
A combination of Diphtheria toxoid, Tetanus toxoid, Pertussis whole cell, Hepatitis B surface antigen and Inactivated polio virus: DTPw$_{SF}$-HB-IPV with addition of the IPV just after T absorbed. This addition method allows IPV adsorption onto $Al(OH)_3$. This vaccine is formulated with the production method 4 (table 5).
A placebo containing only aluminium salts, IPV and buffers of the others antigens. As IPV is the only antigen in this placebo, there is no competition for adsorption. Therefore, IPV is completely absorbed. This vaccine is formulated with the production method 5 (table 5).

The vaccines formulated with production method 2, 3, 4 and 5 were produced with an IPV dose-range between 12.5% and 100% of the standard IPV dose of 40/8/32 IU/0.5 mL.

TABLE 5

Method of productions per 0.5 mL dose

| Step | Method of production 1: DTPw$_{SF}$-HB |
|---|---|
| 1 | Water for injection to reach a final dose volume of 0.5 mL |
| 2 | Add NaCl 1.5M to reach a final concentration of 150 mM |
| 3 | Add 115 µg of $Al^{3+}$ as $AlPO_4$ |
| 4 | Add 10 µg of HBsAg adsorbed |
| 5 | Add 7.5 Lf of Diphtheria toxoid adsorbed |
| 6 | Add 3.25 Lf of Tetanus toxoid adsorbed |
| 7 | Stirring |
| 8 | Adjust the pH at 6.5 +/- 0.1 |
| 9 | Stirring |
| 10 | Add 20IOU Pw adsorbed |
| 11 | Stirring |
| 12 | Store at +2 to +8° C. |

| Step | Method of production 2: IPV standalone |
|---|---|
| 1 | Add IPV at a dose of |

| Type 1 | Type 2 | Type 3 |
|---|---|---|
| 40 IU | 8 IU | 32 IU |
| 20 IU | 4 IU | 16 IU |
| 10 IU | 2 IU | 8 IU |
| 5 IU | 1 IU | 4 IU |

| Step | |
|---|---|
| 2 | Add M199 buffer to reach a final volume of 0.5 mL |
| 9 | Stirring |
| 10 | Adjust the pH at 6.9 +/- 0.2 |
| 14 | Store at +2 to +8° C. |

| Step | Method of production 3: DTPw$_{SF}$-HB-IPV |
|---|---|
| 1 | Water for injection to reach a final dose volume of 0.5 mL |
| 2 | Add NaCl 1.5M to reach a final concentration of 150 mM |
| 3 | Add 115 µg of $Al^{3+}$ as $AlPO_4$ |
| 4 | Add 10 µg of HBsAg adsorbed |
| 5 | Add 7.5 Lf of Diphtheria toxoid adsorbed |
| 6 | Add 3.25 Lf of Tetanus toxoid adsorbed |
| 7 | Stirring |
| 8 | Add IPV at a dose of |

| Type 1 | Type 2 | Type 3 |
|---|---|---|
| 40 IU | 8 IU | 32 IU |
| 20 IU | 4 IU | 16 IU |
| 10 IU | 2 IU | 8 IU |
| 5 IU | 1 IU | 4 IU |

| Step | |
|---|---|
| 9 | Stirring |
| 10 | Adjust the pH at 6.5 +/- 0.1 |
| 11 | Stirring |
| 12 | Add 20IOU Pw adsorbed |
| 13 | Stirring |
| 14 | Store at +2 to +8° C. |

| Step | Method of production 4: DTPw$_{SF}$-HB-IPV |
|---|---|
| 1 | Water for injection to reach a final dose volume of 0.5 mL |
| 2 | Add NaCl 1.5M to reach a final concentration of 150 mM |
| 3 | Add 3.25 Lf of Tetanus toxoid adsorbed |
| 4 | Add IPV at a dose of |

| Type 1 | Type 2 | Type 3 |
|---|---|---|
| 40 IU | 8 IU | 32 IU |
| 20 IU | 4 IU | 16 IU |
| 10 IU | 2 IU | 8 IU |
| 5 IU | 1 IU | 4 IU |

| Step | |
|---|---|
| 5 | Stirring |
| 6 | Add 115 µg of $Al^{3+}$ as $AlPO_4$ |
| 7 | Add 10 µg of HBsAg adsorbed |
| 8 | Add 7.5 Lf of Diphtheria toxoid adsorbed |
| 9 | Stirring |
| 10 | Adjust the pH at 6.5 +/- 0.1 |
| 11 | Stirring |
| 12 | Add 20IOU Pw adsorbed |

TABLE 5-continued

Method of productions per 0.5 mL dose

| 13 | Stirring |
| 14 | Store at +2 to +8° C. |

Method of production 5: Placebo

As per Method of production 3, however all antigens other than IPV have been omitted.

For the method of production 1 formulation: HBsAg, D and T are absorbed separately on $AlPO_4$, $AlPO_4$ and $Al(OH)_3$ respectively. The three antigens are sequentially added to a suspension containing water, NaCl and free $AlPO_4$. The mixture is stirred for 60-75 min. Then the pH is adjusted to 6.5 before addition of absorbed Pw.

For the method of production 3 formulation, the three absorbed antigens are sequentially added to a suspension containing water, NaCl and free $AlPO_4$. The mixture is stirred for 60-75 min before IPV addition. The pH is adjusted to 6.5 before addition of Pw antigens.

For the method of production 4 formulation, T antigen is absorbed on $Al(OH)_3$. Preabsorbed T antigen is added to a suspension containing water and NaCl, followed by IPV types 1, 2 and 3. The mixture is stirred for 60-75 minutes before addition of free $AlPO_4$. Preabsorbed HBsAg is then added, followed by preabsorbed D antigen, and the mixture is then stirred for an additional 60-75 minutes. The pH is adjusted to 6.5 before addition of Pw antigens.

The method of production 3 was eventually selected due to ease of manufacture as this protocol only involved one stirring step. During the process of manufacturing the vaccine, thiomersal is not used, and is not added to the final vaccine product.

The table below presents the composition of the formulations for a 0.5 mL dose.

Determination of Polio Potency on Rats by Seroneutralisation

The potency of the vaccine was determined by a seroneutralisation test after intramuscular inoculation of rats (Sprague-Dawley (OFA) or any beforehand validated strain). Groups of 10 naïve healthy rats were inoculated intramuscularly (0.5 mL) with dilutions of the test samples, reference material in phosphate buffer saline, or diluent (phosphate buffer saline). The ten rats inoculated with the diluent were used as negative controls. Twenty to twenty-two days after the inoculation (immunisation period), each animal was deeply anesthetized prior to blood collection by cardiac puncture. Blood samples were centrifuged (at approximately 800 g), and serums were analysed.

Seroneutralisation Test:

Sera were inactivated by incubation at 56° C. for 30 minutes. Three dilution series of the sera, one for each polio type, were prepared in microplates using the appropriate dilution medium. For the three polio virus types, a predetermined amount of virus was added to the sera dilutions. The three virus suspensions were diluted taking into account their respective titers. The final dilution is called 'working dilution'. Each working dilution was added to the corresponding microplates. Plates were then sealed and incubated at 37° C.±1° C. for 16 hours. Hep-2 cells were then added and microplates were incubated at 37° C.±1° C. for 7 days. The cytopathogenic effect (CPE) of the virus was read using an inverted microscope after Coomassie blue colouration.

The presence of anti-poliomyelitis antibodies inhibits the growth of the virus and the appearance of the corresponding CPE. The anti-polio virus titers (type 1, 2 and 3) correspond to the reciprocal of the last dilution without any CPE.

In each group, animals with neutralising antibodies are recorded and the antibodies titer of each serum sample is determined for the different type of poliovirus. The neutralizing antibody titer is expressed as the $\log_2$ of the inverse of

TABLE 6

| Description | $Al^{3+}$ as $AlPO4$ for D adsorption | $Al^{3+}$ as $Al(OH)3$ for D adsorption | $Al^{3+}$ as $AlPO4$ for HBsAg adsorption | $Al^{3+}$ as $AlPO4$ for Pw adsorption | Free $AlPO4$ | Free $Al(OH)3$ | Diphtheria toxoid dose | Tetanus toxoid dose | Pertussis dose | HBsAg dose | IPV dose % of standard dose | IPV dose D-antigen units (*) (T1/T2/T3) |
|---|---|---|---|---|---|---|---|---|---|---|---|---|
| Method of production 1 DTPw$_{SF}$-HB | 75 µg | 70 µg | 200 µg | 170 µg | 115 µg | NA | 7.5Lf | 3.25Lf | 20IOU | 10 µg | NA | NA |
| Method of production 2 IPV | NA | NA | NA | NA | NA | NA | NA | NA | NA | NA | 100% 50% 25% 12.50% | 40/8/32 20/4/16 10/2/8 5/1/4 |
| Method of production 3 DTPw$_{SF}$-HB-IPV | 75 µg | 70 µg | 200 µg | 170 µg | 115 µg | NA | 7.5Lf | 3.25Lf | 20IOU | 10 µg | 100% 50% 25% 12.50% | 40/8/32 20/4/16 10/2/8 5/1/4 |
| Method of production 4 DTPw$_{SF}$-HB-IPV | 75 µg | 70 µg | 200 µg | 170 µg | 115 µg | NA | 7.5Lf | 3.25Lf | 20IOU | 10 µg | 100% 50% 25% 12.50% | 40/8/32 20/4/16 10/2/8 5/1/4 |
| Method of production 5 Placebo | NA | NA | NA | NA | 560 µg | 70 µg | NA | NA | NA | NA | 100% 50% 25% 12.50% | 40/8/32 20/4/16 10/2/8 5/1/4 |

(*) The D-antigen content is the values targeted for the dilution of the concentrated inactivated polio bulk during the formulation the highest dilution of the serum sample that totally inhibits the cytopathic effect of poliovirus on Hep-2 cells. The geometric mean titer per dilution (GMT) and per virus type is then determined for each group of rats.

For each type of virus, the vaccine dilution and subsequently the amount of D-antigen which induced neutralising antibodies in 50% of the rats (ED50) was also calculated by probit analysis. The ED50 was expressed in D-antigen units.

In order to quantify the potency relative to that of the reference vaccine (usually Poliorix®, but may be a DTPaH-BIPV vaccine such as Pediarix®), the relative potency (RP) defined as the ratio of two equivalent dose responses in a multi-dose test was measured. In this approach, the potency of the test vaccine is calculated by parallel line assay as described in Finney, 1978 (Statistical Method in Biological Assay, Charles Griffin & Company Ltd, London, 1978).

Determination of the Potency Polio Type 1, 2 and 3 by ELISA

The determination of the potency Polio by ELISA is performed in one or two steps depending on whether measurement is being carried out on bulk unabsorbed IPV vs formulated vaccines respectively:

1. Desorption for final absorbed vaccine (for measuring D-antigen units in formulated vaccines—not required for measurement in unabsorbed IPV antigen bulk);
2. ELISA test for the quantification of D-antigen content of desorbed and unabsorbed vaccine and/or polio bulk Desorption Step After centrifugation for 10 minutes of the absorbed vaccine under test, three successive desorptions are performed, by adding a desorption phosphate buffer to the pellet, mixing and incubating at room temperature. The first and the second desorption periods are of 2 hours, the incubation period for the third extraction being one night at room temperature. The harvests from the three extractions are pooled and diluted with phosphate buffer solution (PBS) without Ca and Mg containing bovine serum albumine (BSA) and Tween 20.

The three poliovirus antigens are quantified by ELISA as described below.

D-Antigen Quantification by ELISA:

Microtiter plates are coated with specific rabbit anti-polio virus (type 1, 2 or 3) IgG, diluted with carbonate/bicarbonate buffer (pH 9.6), and incubated overnight at 4° C. After washing, the saturating solution (phosphate buffer saline w/o Ca and Mg+1% BSA) is added. Blanks (PBS) and serial dilutions of vaccine samples and in-house unabsorbed standard are added in duplicate. The in house trivalent standard preparation contains calibrated type 1, 2 and 3 antigens. The calibrator is the European Pharmacopoeia Biological reference (EP-BRP).

For all following steps, the microtiter plates are incubated during 1 h30 at 37° C. and washed. Rabbit anti-polio virus (type 1, 2 or 3) IgG conjugated to peroxydase, diluted with phosphate buffer (w/o Ca and Mg+Tween 20) containing BSA, is added. The substrate solution, containing the tetramethylbenzidine dissolved in dimethyl sulfoxide (DMSO) and diluted in acetate buffer containing 0.003% $H_2O_2$, is added, followed by a 15-30 minutes incubation in the dark. The blocking solution, containing $H_2SO_4$, is then added. Within one hour, the optical density (O.D.) of each well is read using a photometer set at 450 nm with a reference at 620 nm.

The D-antigen concentration in test samples is calculated from the standard curve obtained by plotting the O.D. values against the standard antigen concentrations.

As a supplement to the Potency by ELISA, any unabsorbed IPV antigen may be detected by the completeness method:

Completeness of Adsorption to Adjuvant Unbound Polio Type 1, 2 and 3 by Elisa

Two successive centrifugations are performed. The supernatant is then harvested and tested undiluted in duplicate on microplates by ELISA. Microtiter plates are coated with specific rabbit anti-polio virus (type 1, 2 or 3) IgG, diluted with carbonate/bicarbonate buffer (pH 9.6), and incubated overnight at 4° C. After washing, the saturating solution (phosphate buffer saline w/o Ca and Mg+1% BSA) is added. Blanks (PBS), supernatant and in-house unabsorbed standard are added in duplicate.

For all following steps, the microtiter plates are incubated during 1 h30 at 37° C. and washed. Rabbit anti-polio virus (type 1, 2 or 3) IgG conjugated to peroxydase, diluted with phosphate buffer (w/o Ca and Mg+Tween 20) containing BSA, is added. The substrate solution, containing the tetramethylbenzidine dissolved in dimethyl sulfoxide (DMSO) and diluted in acetate buffer containing 0.003% $H_2O_2$, is added, followed by a 15-30 minutes incubation in the dark. The blocking solution, containing $H_2SO_4$, is then added. Within one hour, the optical density (O.D.) of each well is read using a photometer set at 450 nm with a reference at 620 nm.

The completeness is considered positive (antigen in the supernatant) if the mean OD of sample is higher than the mean OD values of blanks+3 standard deviations and if the mean OD of sample is higher than 0.1.

In case of positive completeness, the antigen content is measured by ELISA method as described in the second step of the Potency Polio Type 1, 2 and 3 by ELISA.

Method of measuring International Opacity Unit (IOU)

Cell concentration (IOU) can be determined using either visual IRPO (International Reference Preparation of Opacity) standard solution or by absorbance measurement at 660 nm.

The opacity of Single Strain Suspension is then determined by applying the "assigned opacity" equation as follows:

$$AO=LO/KO\times CO;$$

where AO=assigned opacity, LO=live harvest opacity, KO=killed harvest opacity, and CO=concentrate opacity.

Results

Determination of Potency Polio on Rats by Seroneutralisation at the Standard 40:8:32 Dose Experiments were performed to determine the potency of IPV types 1, 2 and 3. Results are shown in Table 8 below (in the present document, 40:8:32 D-antigen units of IPV types 1, 2 and 3 respectively is equivalent to 100% IPV dose).

TABLE 8

Potency of IPV types 1, 2 and 3 in three different vaccine formulations.

| Decription | Potency IPV (ED50 expressed in IU/dose) | | |
|---|---|---|---|
| | Type 1 | Type 2 | Type 3 |
| Ref. Poliorix | 20.78 | 8.88 | 40.02 |
| Ref. DTPaHBIPV | 3.21 | 0.57 | 8.62 |
| DTPw$_{SF}$-HB-IPV Method of production 3 | <1.93 | 0.64 | <2.57 |

The DTPw$_{SF}$-HB-IPV formulation (100% IPV) presents IPV potencies better than the reference Poliorix and similar or better than the reference DTPaHBIPV.

Evaluation of IPV Potency with Reduced IPV Dosages

The potency is measured by in vitro and in vivo methods described above. The potency by Elisa of reduced dose IPV for both formulations of methods of production 3 and 4 was examined in vitro and compared with reference DTPaIPVHB as shown in Table 9. Two batches for each formulation were tested for method of production 3.

The percentage of recovery was calculated with regard to the antigen content taken from IPV bulk for each formulation (e.g. 40/8/32 for 100% IPV containing formulation; 20/8/16 for 50% IPV containing formulation; 10/4/8 for 25% IPV containing formulation; 5/2/4 for 12.5 IPV containing formulation)

TABLE 9

| | T1 | | T2 | | T3 | |
|---|---|---|---|---|---|---|
| Sample | Potency Polio (% Recovery) | Completness (% Recovery) | Potency Polio (% Recovery) | Completness (% Recovery) | Potency Polio (% Recovery) | Completness (% Recovery) |
| DTPaIPVHB Reference | 82% | NP | 99% | NP | 93% | NP |
| DTPwSF-HB-IPV 1 "Method of Production 3" 100% IPV | 46% | 47% | 94% | <5% | 24% | 74% |
| DTPwSF-HB-IPV 2 "Method of Production 3" 100% IPV | 80% | <5% | 100% | <5.0% | 81% | 17% |
| DTPwSF-HB-IPV 1 "Method of Production 3" 50% IPV | 48% | 31% | 98% | <5% | 29% | 64% |
| DTPwSF-HB-IPV 2 "Method of Production 3" 50% IPV | 71% | <5% | 99% | <5% | 91% | >5% |
| DTPwSF-HB-IPV 1 "Method of Production 3" 25% IPV | 54% | 34% | 115% | <5% | 33% | 71% |
| DTPwSF-HB-IPV 2 "Method of Production 3" 25% IPV | 81% | <5% | 115% | <5% | 107% | <5% |
| DTPwSF-HB-IPV "Method of Production 3" 12.5% IPV | 50% | 24% | 110% | <5% | 28% | 60% |
| DTPwSF-HB-IPV "Method of Production 4" 100% IPV | 41% | 48% | 93% | <5% | 23% | 51% |
| DTPwSF-HB-IPV "Method of Production 4" 50% IPV | 47% | 37% | 98% | <5% | 28% | 69% |
| DTPwSF-HB-IPV "Method of Production 4" 25% IPV | 51% | 28% | 80% | <5% | 33% | 61% |
| DTPwSF-HB-IPV "Method of Production 4" 12.5% IPV | 42% | 22% | 100% | <5% | 40% | 58% |
| Placebo "Method of production 5" 100% IPV | 86% | <5% | 98% | <5% | 107% | <5% |
| Placebo "Method of production 5" 50% IPV | 94% | <5% | 110% | <5% | 111% | <5% |
| Placebo "Method of production 5" 25% IPV | 80% | <5% | 100% | <5% | 104% | <5% |
| Placebo "Method of production 5" 12.5% IPV | 72% | <5% | 100% | <5% | 98% | <5% |

Table 9 show that the adsorption completeness is similar for all IPV doses. The Type 1 and Type 3 are strongly desorbed (17%-74%) while the Type 2 stay well absorbed. The three types are well absorbed for the placebo formulation for all the IPV doses. The adsorption is similar as for DTPaIPVHB reference vaccine.

There is a variability IPV completeness because of the fact that the completeness quantification method is not validated neither for DTPwHB IPV formulations nor for lower IPV concentrations (<40/8/32 D-antigen Units/0.5 ml).

Figure 1:
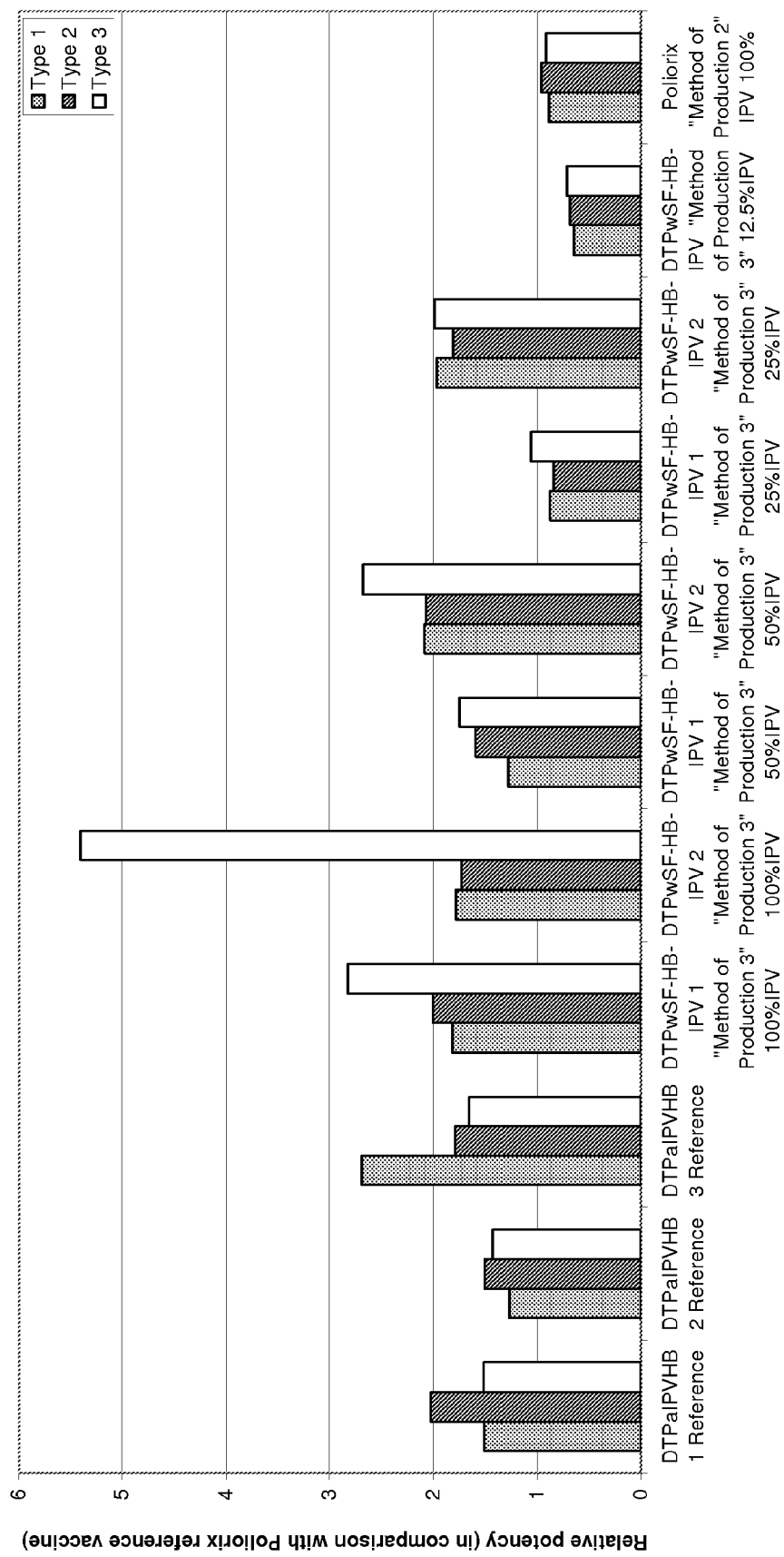
FIG. 1. Evolution of the Relative Potency (RP) of DTPw$_{SF}$-HB-IPV "Method of production 3" with the IPV dose.

The relative potency (expressed in comparison with reference poliorix vaccine) of reduced dose IPV for both formulations of methods of production 3 and 4 was examined in vivo in comparison with reference formulations as shown in FIGS. 1 and 2. Two batches for each formulations were tested for method of production 3.

FIG. 1 shows that the IPV potency of DTPw$_{SF}$-HB-IPV with 100% IPV is slightly greater than the potency of IPV in DTPaHBIPV. The IPV potency of DTPw$_{SF}$-HB-IPV 50% from the formulation of method of production 3 can be seen to be similar to DTPaHBIPV 100%. The IPV potency for DTPw$_{SF}$-HB-IPV 25% of method of production 3 is slightly lower than for Poliorix®. It was also found that 12.5% of the IPV dose was not sufficient to obtain a good IPV potency.

FIG. 2 shows that the IPV potency is similar for the formulation of method of production 3 and the formulation of method of production 4. It is also shown that there is a trend of better potency for the placebo than for DTPw$_{SF}$-HB-IPV.

These data therefore confirm that a reduced dose of IPV is sufficient to obtain a good potency in vivo.

Example 2

Feasibility of Using No Thiomersal in Vaccines of the Invention

The Preservative Efficacy Test (PET) allows the demonstration of the antimicrobial activity of the tested vaccine. The test consists in:
- challenging the vaccine preparation, in its final container step, with a prescribed inoculum of suitable micro-organisms,
- storing the inoculated preparation at a prescribed temperature
- withdrawing samples from the container at specified intervals of time and counting the organisms in the taken samples.

The PET testing procedure is described in the European Pharmacopoeia (5.1.3) and in the USP (<51>). According to these guidelines, the antimicrobial activity is evaluated by comparing the reduction in the number of viable micro-organisms with the criteria mentioned in the following table (Table 7)

TABLE 7

| EP and USP Criteria | | | | | |
|---|---|---|---|---|---|
| | | Criteria: log reduction | | | |
| Microorganisms | Time | EP A | EP B | EP C | USP |
| Bacteria | | | | | |
| Staphylococus aureus | 6 h | 2 | | | |
| Escherichia coli | d 1 | 3 | 1 | Ni* | |
| Pseudomonas aeruginosa | d 7 | | 3 | Ni* | 1 |
| | d 14 | | | 3 | 3 |
| | d 28 | Nr* | Ni* | Ni* | Ni* |
| Yeast and moulds | | | | | |
| Candida albicans | d 7 | 2 | | | Ni* |
| Aspergillus niger | d 14 | | 1 | Ni* | Ni* |
| | d 28 | Ni* | Ni* | Ni* | Ni* |

Nr*: not recovered
Ni*: not increased

Example 3

Effect of Hib Component on the Potency of IPV and Stability of IPV Over Time

Relative potency of IPV was measured as described in Example 1 to determine the effects the Hib component may have on IPV potency and to evaluate the stability of IPV over time at different IPV doses. The vaccines investigated were DTPwHBIPV(40-8-32), DTPwHBIPV with reconstituted Hib and stored for 8 months, DTPwHBIPV(20-4-16), DTPwHBIPV(20-4-16) with reconstituted Hib and stored for 8 months, DTPwHBIPV(20-4-16) and stored for 8 months, DTPwHBIPV(10-2-8) and DTPwHBIPV(10-2-8) with reconstituted Hib and stored for 8 months. RP values were measure relative to DTPaIPVHB (Pediarix) (FIG. 3a) or Poliorix (FIG. 3b). It was found that the Hib component has no impact on IPV potency. The relative potency of IPV was found to be maintained at 8 months (FIG. 3).

Example 4

Effect of AlPO4/Al(OH)3 Ratio on the Visual Aspect, the Adsorption of D and T and the Potency of IPV Formulations were performed with change of Aluminium composition.

The formulations DTPw$_{SF}$-HB-IPV usually contains 630 μg Aluminium: 560 μg Al$^{3+}$ as AlPO4, 70 μg Al3+ as Al(OH)$_3$. Aluminium salts are used to adsorb D, T, Pw and HBsAg. 115 μg Al$^{3+}$ of free AlPO$_4$ is added during the formulation.

Formulations were performed with the following ratios of free Al$^{3+}$:

TABLE 10

AlPO4/Al(OH)3 ratio

|  | Al(OH)3 μg Al3+ | AlPO4 μg Al3+ |
|---|---|---|
| Lot 1 | 0 | 115 |
| Lot 2 | 23 | 92 |
| Lot 3 | 69 | 46 |
| Lot 4 | 46 | 69 |
| Lot 5 | 92 | 23 |
| Lot 6 | 115 | 0 |

TABLE 11

Method of production for DTPwHB-IPV

| Step | Method of production 3: DTPw$_{SF}$-HB-IPV |
|---|---|
| 1 | Water for injection to reach a final dose volume of 0.5 mL |
| 2 | Add NaCl 1.5M to reach a final concentration of 150 mM |
| 3 | Add 115 μg of Al$^{3+}$ with at the different ratios Al(OH)$_3$/AlPO$_4$ |
| 4 | Add 10 μg of HBsAg adsorbed |
| 5 | Add 7.5 Lf of Diphtheria toxoid adsorbed |
| 6 | Add 3.25 Lf of Tetanus toxoid adsorbed |
| 7 | Stirring |
| 8 | Add IPV at a dose of 40/8/32 IU |
| 9 | Stirring |
| 10 | Adjust the pH at 6.5 +/− 0.1 |
| 11 | Stirring |
| 12 | Add 20IOU Pw adsorbed |
| 13 | Stirring |
| 14 | Store at +2 to +8° C. |

Visual aspect was observed and up to ratio 69/46, acceptable aggregation is obtained.

Formulations were performed with the same production method and a dose-range for IPV between 0 and 100% of the regular IPV dose.

The percentage of D and T toxoids adsorption was measured by ELISA. The stability of the adsorption was followed by a treatment of 7 days at 37° C. Results are presented in Table 12 and 14.

TABLE 12

Percentage of D toxoid desorption in DTPwHB-IPV with IPV dose-range

| | | RATIO Al(OH)$_3$/AlPO$_4$ | | | | | |
|---|---|---|---|---|---|---|---|
| | | 0/115 | | 23/92 | | 46/69 | |
| | IPV dose | T0 | 7 d 37° C. | T0 | 7 d 37° C. | T0 | 7 d 37° C. |
| Pw$_{SF}$ | 0% | <1% | 25% | <1% | 6% | / | |
| | 25% | <1% | 29% | <1% | 15% | <1% | 5% |
| | 50% | 3% | 41% | <1% | 26% | <1% | 17% |
| | 100% | 4% | 49% | <1% | 23% | <1% | 11% |

TABLE 13

Percentage of T toxoid desorption in DTPwHB-IPV with IPV dose-range

| | | RATIO Al(OH)$_3$/AlPO$_4$ | | | | | |
|---|---|---|---|---|---|---|---|
| | | 0/115 | | 23/92 | | 46/69 | |
| | IPV dose | T0 | 7 d 37° C. | T0 | 7 d 37° C. | T0 | 7 d 37° C. |
| Pw$_{SF}$ | 0% | <1% | 34% | <1 | 12% | / | |
| | 25% | <1% | 50% | <1 | 32% | <1% | 12% |
| | 50% | 5% | 61% | <1 | 51% | <1% | 33% |
| | 100% | 8% | 63% | <1 | 41% | <1% | 29% |

IPV adsorption was followed. The stability of the adsorption was followed by a treatment of 21 days at 25° C.

TABLE 14

Percentage of IPV desorption in DTPwHB-IPV with IPV dose-range

| | | Estimation of Ag not adsorbed RATIO Al(OH)3/AlPO4 | | | | | |
|---|---|---|---|---|---|---|---|
| IPV | | 0/115 | | 23/92 | | 46/69 | |
| Dose | Type | T0 | 21 d 25° C. | T0 | 21 d 25° C. | T0 | 21 d 25° C. |
| 0% | N/A | N/A | N/A | N/A | N/A | AGGREGATION | |
| 25% | Type 1 | ~10-20% | ~20-30% | ~10-20% | ~20-30% | <10% | ~20-30% |
| | Type 2 | <10% | <10% | <10% | <10% | <10% | <10% |
| | Type 3 | >30% | >30% | ~20-30% | >30% | <10% | >30% |
| 50% | Type 1 | >30% | >30% | ~10-20% | >30% | ~10-20% | >30% |
| | Type 2 | ~10-20% | ~10-20% | <10% | <10% | <10% | <10% |
| | Type 3 | >30% | >30% | ~10-20% | >30% | ~10-20% | >30% |
| 100% | Type 1 | >30% | >30% | ~10-20% | >30% | ~10-20% | >30% |
| | Type 2 | ~10-20% | ~10-20% | <10% | <10% | <10% | <10% |
| | Type 3 | >30% | >30% | ~20-30% | >30% | ~20-30% | >30% |

The increase of the Al(OH)$_3$ content in the formulations allows an adsorption improvement for D, T and IPV.

The better adsorption ratio obtained was with the Al(OH)$_3$/AlPO$_4$ ratio of 46/69.

At this ratio:

The T and D adsorption is complete in T0. Desorption after an accelerated stability study of 7 days at 37° C. present <20% of desorption for D, <30% for T.

Each IPV type is absorbed. Desorption of the Type 3 occurs 21 days at 25° C.

The formulations with the ratio 46/69 were tested in-vivo and compared with Tetravac, Poliorix and a DTPaIPV vaccine.

TABLE 15

In-vivo potencies results

| Sample | ED50 | | |
|---|---|---|---|
| | Type 1 | Type 2 | Type 3 |
| DTPw-HB-IPV 100%/HIB Ratio 46/69 | <1.93 | <0.64 | 2.57 |
| DTPw-HB-IPV 50%/HIB Ratio 46/69 | <1.59 | 0.46 | <1.67 |
| DTPw-HB-IPV 25%/HIB Ratio 46/69 | 3.08 | 0.96 | 3.25 |
| Tetravac | 8.53 | 0.39 | 9.15 |
| Poliorix | 9.52 | 2.64 | 15.06 |
| DTPaHBIPV | <5.18 | <0.64 | 15.01 |

There are no significant differences (ED50) between the DTPw-HB-IPV formulations. DTPaHBIPV, Tetravac and Poliorix give similar results, inferior to the DTPw-HB-IPV formulations (except for the type 2 for which all the formulations are equivalent).

Example 5

Clinical Evaluation of the Investigational DTPw-HBV-IPV/Hib Vaccine with Reduced IPV Dosages A Phase II, feasibility study is planned to assess the immunogenicity, reactogenicity and safety of three different formulations of GSK Biologicals' investigational DTPw-HBV-IPV/Hib vaccine as compared to the commercial DTPw-HBV/Hib and IPV vaccines administered concomitantly.

Indication/Populations:

Primary immunization of healthy infants in the first week of life against diphtheria, tetanus, pertussis, hepatitis B, poliomyelitis and *Haemophilus influenzae* type b diseases.

Study Groups:

DTPw-HBV-IPV(standard dose)/Hib vaccine
DTPw-HBV-IPV(49% of standard dose)/Hib vaccine
DTPw-HBV-IPV(26% of standard dose)/Hib vaccine
DTPw-HBV/Hib+IPV vaccines Co-Primary Objectives:

The co-primary objectives will be assessed in sequential manner: i.e. the second and third objectives will be assessed only if the preceding one has been met.

To demonstrate the non-inferiority of the DTPw-HBV-IPV (standard dose)/Hib vaccine to the IPV vaccine co-administered with the DTPw-HBV/Hib vaccine in terms of antibody response to the three poliovirus types, one month after the primary vaccination course.

The objective of non-inferiority will be reached if the upper limit of the standardised asymptotic 95% CI on the difference between groups (DTPw-HBV/Hib+IPV minus DTPw-HBV-IPV(standard dose)/Hib) in terms of seroprotection rates for each of the three poliovirus types is ≤10%.

To demonstrate the non-inferiority of the DTPw-HBV-IPV (49% of standard dose)/Hib vaccine to the IPV vaccine co-administered with the DTPw-HBV/Hib vaccine in terms of antibody response to the three poliovirus types, one month after the primary vaccination course.

The objective of non-inferiority will be reached if the upper limit of the standardised asymptotic 95% CI on the difference between groups (DTPw-HBV/Hib+IPV minus DTPw-HBV-IPV(49% of standard dose)/Hib) in terms of seroprotection rates for each of the three poliovirus types is ≤10%.

To demonstrate the non-inferiority of the DTPw-HBV-IPV (26% of standard dose)/Hib vaccine to the IPV vaccine co-administered with the DTPw-HBV/Hib vaccine in terms of antibody response to the three poliovirus types, one month after the primary vaccination course.

The objective of non-inferiority will be reached if the upper limit of the standardised asymptotic 95% CI on the difference between groups (DTPw-HBV/Hib+IPV minus DTPw-HBV-IPV(26% of standard dose)/Hib) in terms of seroprotection rates for each of the three poliovirus types is ≤10%.

Secondary Objectives:

Immunogenicity

To assess the immunogenicity the DTPw-HBV-IPV/Hib candidate vaccine in terms of response to all vaccine antigens in comparison with the DTPw-HBV/Hib and IPV vaccines co-administered.

Reactogenicity

To assess the reactogenicity and safety of the study vaccines, in terms of solicited symptoms, unsolicited symptoms and serious adverse events.

Vaccination Schedule

Three-dose primary vaccination schedule at 6, 10 and 14 weeks of age. All subjects receive a birth dose of Hepatitis B.

Country:

Philippines

Blood Sampling:

Pre- and post-vaccination 3

Vaccine Formulations:

TABLE 16

Vaccine formulations

| Vaccine | Formulation/dose | Presentation | Volume |
|---|---|---|---|
| GSK Biologicals' DTPw-HBV-IPV/Hib | Diphtheria toxoid: not less than 30 IU (7.5 Lf)<br>Tetanus toxoid: not less than 60 IU (3.25 Lf)<br>*Bordetella pertussis*, killed: not less than 4 IU (20 OU)<br>r-DNA HBsAg: 10 µg<br>Aluminium as salts: 0.66 mg | Whitish liquid in monodose vials | 0.5 ml of the reconstituted vaccine |

TABLE 16-continued

Vaccine formulations

| Vaccine | Formulation/dose | Presentation | Volume |
|---|---|---|---|
| IPV component (standard dose) | Inactivated Poliovirus type 1: 40 D antigen units<br>Inactivated Poliovirus type 2: 8 D antigen units<br>Inactivated Poliovirus type 3: 32 D antigen units | | |
| IPV component (49% of standard dose) | 49% of full standard dose IPV (40-8-32) | | |
| IPV component (26% of standard dose) | 26% of full standard dose IPV (40-8-32) | | |
| | Conjugate of *Haemophilus influenzae* type b capsular polysaccharide: 2.5 µg<br>and Tetanus toxoid: 5-10 µg<br>Lactose: 12.6 mg<br>Aluminium as salts: 30 µg | Freeze-dried pellet in monodose vials | |
| GSK Biologicals' DTPw-HBV/Hib (Zilbrix ™ Hib) | Diphtheria toxoid: not less than 30 IU (7.5 Lf)<br>Tetanus toxoid: not less than 60 IU (3.25 Lf)<br>*Bordetella pertussis*, killed: not less than 4 IU (20 OU)<br>r-DNA HBsAg: 10 µg<br>Aluminium as salts: 0.66 mg<br>Thiomersal: 8 µg | Whitish liquid in two-dose vials | 1 ml of the reconstituted vaccine |
| | Conjugate of *Haemophilus influenzae* type b capsular polysaccharide: 2.5 µg and Tetanus toxoid: 5-10 µg<br>Lactose: 12.6 mg<br>Aluminium as salts: 30 µg | Freeze-dried pellet in two-dose vials | |
| GSK Biologicals' IPV (Poliorix ™) | Inactivated Poliovirus type 1: 40 D antigen units<br>Inactivated Poliovirus type 2: 8 D antigen units<br>Inactivated Poliovirus type 3: 32 D antigen units<br>2-phenoxyethanol max 2.5 mg<br>Polysorbate max 50 µg<br>Formaldehyde max 100 µg<br>Phosphate buffered saline<br>Contains amino acids for injection q.s, ad 0.5 ml | Whitish liquid in monodose vials | 0.5 ml |

Pre-Adsorption of the Antigens

The DTPw-HBV-IPV formulation combines diphtheria toxoid, tetanus toxoid, three *Bordetella pertussis* strains, the purified major surface antigen (HBsAg) of the Hepatitis B virus (HBV) and the inactivated polio virus (IPV). These antigens, except IPV, were first pre-absorbed on aluminium salt before being mixed with aluminium salt, sodium chloride buffer and water for injection.

Adsorption of Diphtheria Toxoid

The diphtheria purified concentrate was absorbed on aluminium phosphate in a ratio of 15 Lf Diphtheria toxoid/0.15 mg $Al_{3+}$. The two components were stirred for 15 up to 45 minutes at room temperature. The pH was adjusted to pH 5.1±0.1, followed by stirring for 15 up to 45 minutes. The mix was stored for one week at 37° C. After stirring of 15 up to 45 minutes at room temperature, the pH was adjusted to pH 6.1±0.1. The absorbed concentrate was stored at +2° C.-+8° C. for at least 7 days before final formulation of DTPw-HB-IPV vaccine. FIG. 1 hereafter highlights the adsorption manufacturing process of the pre-absorbed Diphtheria bulk.

Adsorption flowchart diphtheria toxoid $AlPO_4$
↓
D(15 Lf/0.15 mg $Al_{3+}$)
↓
↓

-continued

Stirring 15 up to 45 minutes at room temperature
↓
Adjust and check pH (5.1 ± 0.1)
↓
Stirring 15 up to 45 minutes at room temperature
↓
Adsorption 7 days at 37° C.
↓
Stirring 15 up to 45 minutes at room temperature
↓
Adjust and check pH (6.1 ± 0.1)
↓
Store minimum 7 days AT +2° C. +8° C. before formulation Adsorption of Tetanus Toxoid The purified tetanus concentrate was absorbed on aluminium hydroxide in a ratio of 3.25 Lf/0.07 mg $Al^{3+}$. The two components were stirred for 15 up to 20 minutes. The pH was adjusted at pH 6.1±0.1. The mix was stored under stirring for 16 up to 24 hours at room temperature. A sodium chloride solution of 1500 mM of nominal concentration was added (ad 150 mM). After stirring of 15 up to 45 minutes at room temperature, the pH was adjusted to 6.1±0.1. The absorbed concentrate was stored at +2° C.-+8° C. for at least 14 days before final formulation of DTPw-HBV-IPV vaccine.

Adsorption flowchart of tetanus toxoid

Al(OH)$_3$
↓
T (3.25 Lf/0.07 mg Al$_{3+}$)
↓
Stirring 15 up to 20 minutes at room temperature
↓
Adjust and check pH 6.1 ± 0.1
↓
Stirring 16 hours up to 24 hours at room temperature
↓
NaCl 1500 mM (ad 150 mM)
↓
Stirring 15 up to 45 minutes at room temperature
↓
Adjust and check pH (6.1 ± 0.1)
↓
Store minimum 14 days at +2° C. +8° C. before formulation Adsorption of Hepatitis B Antigen The sterile purified HBsAg bulk was mixed with a sterile suspension of aluminium phosphate in order to obtain a suspension which contains per 10 μg HBsAg, 0.2 mg Al$^{3+}$ (as aluminium phosphate), 150 mM NaCl in a final volume of about 50 μl.

Adsorption procedure of HBsAg

HBsAg (10 μg/0.5 ml)
↓
Al$_{3+}$(0.2 mg/0.5 ml)(AlPO$_4$)
↓
Stirring 15-20 minutes at room temperature
↓

-continued

Adjust and check pH (5.3 ± 0.2)
↓
Stirring 16-24 hours at room temperature
↓
Adjust pH at 6.1 ± 0.1
↓
Store 14 days at room temperature
↓
Storage at 4° C.

Adsorption of Pw Antigen

The AlPO$_4$ solution was transferred aseptically into a sterile vessel. The solution was stirred for 5 to 10 minutes and the pH was adjusted to 6.5+/−0.1 with 1M HCl or 0.5M NaOH directly in the vessel. The solution was stirred for 15-20 minutes. The pH was checked (6.5+/−0.1) and adjusted if necessary.

Before the adsorption, the pertussis pooled harvest (PPH) was mixed for a minimum of 15 minutes prior to use and then the PPH was added into the sterile vessel containing the AlPO$_4$. The suspension was stirred for minimum 15 minutes at room temperature and could be stored overnight at room temperature. If the product was stored overnight at room temperature, it had to be resuspended for minimum 30 minutes before distribution. Samples were taken for testing.

The Pw absorbed bulk was distributed into sterile glass bottles and stored at 2-8° C.

Flow chart of Pw adsorption

Transfer AlPO$_4$ in sterile stainless steel vessel
↓
Adjust pH to 6.5/0.1
↓
Stirring 15-20 minutes at room temperature
↓
Check pH and adjust if necessary (6.5 +/- 0.1)
↓
Add the PPH in the sterile stainless steel vessel
↓
Stirring min. 15 minutes at room temperature
↓

-continued

Distribution in glass bottle

↓

Storage of the Pw adsorbed at 2-8° C.

DTPW-HBV-IPV Final Formulation

The process was done as follows:

The sodium chloride solution and water were mixed for injections in order to achieve a final concentration of 150 mM NaCl.

AlPO$_4$ was added in order to obtain a free Al$^{3+}$ concentration of 0.115 mg/dose The absorbed HEF, diphtheria and tetanus concentrates were added in order to obtain a final concentration of 10 μg of HBsAg, 7.5 Lf diphtheria toxoid and 3.25 Lf tetanus toxoid per 0.5 ml dose.

IPV was added in order to obtain a final concentration of 40/8/32 or 19.6/3.9/15.7 or 10.4/2.1/8.3 UI/d.

Stirring gently for 60 up to 120 minutes at room temperature.

pH was adjusted at 6.5+/−0.1

Stirring for 15 up to 20 minutes at room temperature.

pH was checked: 6.5+/−0.1

Absorbed Pw concentrate was added in order to obtain a final concentration of 20 IOU per 0.5 ml dose Stirring for 15 to 45 minutes at room temperature.

pH was measured

The final bulk was stored between +2° C. and +8° C. until filling.

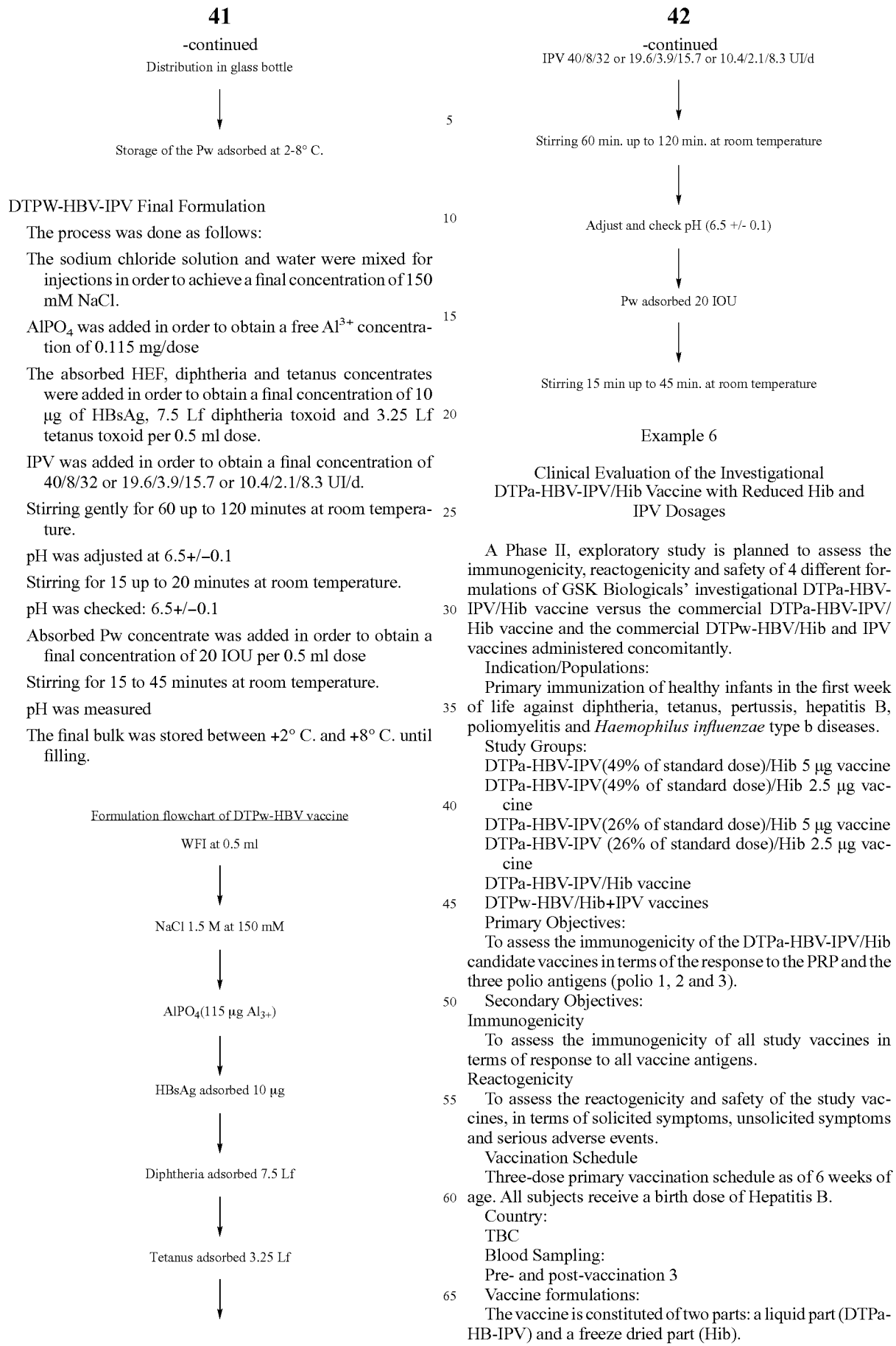

Formulation flowchart of DTPw-HBV vaccine

WFI at 0.5 ml

↓

NaCl 1.5 M at 150 mM

↓

AlPO$_4$(115 μg Al$_{3+}$)

↓

HBsAg adsorbed 10 μg

↓

Diphtheria adsorbed 7.5 Lf

↓

Tetanus adsorbed 3.25 Lf

↓

IPV 40/8/32 or 19.6/3.9/15.7 or 10.4/2.1/8.3 UI/d

↓

Stirring 60 min. up to 120 min. at room temperature

↓

Adjust and check pH (6.5 +/− 0.1)

↓

Pw adsorbed 20 IOU

↓

Stirring 15 min up to 45 min. at room temperature

Example 6

Clinical Evaluation of the Investigational DTPa-HBV-IPV/Hib Vaccine with Reduced Hib and IPV Dosages A Phase II, exploratory study is planned to assess the immunogenicity, reactogenicity and safety of 4 different formulations of GSK Biologicals' investigational DTPa-HBV-IPV/Hib vaccine versus the commercial DTPa-HBV-IPV/Hib vaccine and the commercial DTPw-HBV/Hib and IPV vaccines administered concomitantly.

Indication/Populations:

Primary immunization of healthy infants in the first week of life against diphtheria, tetanus, pertussis, hepatitis B, poliomyelitis and *Haemophilus influenzae* type b diseases.

Study Groups:
DTPa-HBV-IPV(49% of standard dose)/Hib 5 μg vaccine
DTPa-HBV-IPV(49% of standard dose)/Hib 2.5 μg vaccine
DTPa-HBV-IPV(26% of standard dose)/Hib 5 μg vaccine
DTPa-HBV-IPV (26% of standard dose)/Hib 2.5 μg vaccine
DTPa-HBV-IPV/Hib vaccine
DTPw-HBV/Hib+IPV vaccines Primary Objectives:

To assess the immunogenicity of the DTPa-HBV-IPV/Hib candidate vaccines in terms of the response to the PRP and the three polio antigens (polio 1, 2 and 3).

Secondary Objectives:

Immunogenicity

To assess the immunogenicity of all study vaccines in terms of response to all vaccine antigens.

Reactogenicity

To assess the reactogenicity and safety of the study vaccines, in terms of solicited symptoms, unsolicited symptoms and serious adverse events.

Vaccination Schedule

Three-dose primary vaccination schedule as of 6 weeks of age. All subjects receive a birth dose of Hepatitis B.

Country:
TBC

Blood Sampling:
Pre- and post-vaccination 3

Vaccine formulations:
The vaccine is constituted of two parts: a liquid part (DTPa-HB-IPV) and a freeze dried part (Hib).

D, T, PT, FHA, PRN and HBsAg are preliminary pre-absorbed. Water and NaCl are blended with the different antigens. The mixture is stirred to homogenize and pH is adjusted. The final composition of the DTPa-HB-IPV part of the vaccine is presented in the table hereafter.

TABLE 17

Composition for one 0.5 mL human dose of DTPa-HBV-IPV

| Component | Amount |
|---|---|
| D toxoid | 25Lf |
| T toxoid | 10Lf |
| PT | 25 µg |
| FHA | 25 µg |
| PRN | 8 µg |
| HBsAg | 10 µg |
| IPV type 1 | 40 or 19.6 or 10.4 IU |
| IPV type 2 | 8 or 3.9 or 2.1 IU |
| IPV type 3 | 32 or 15.7 or 8.3 IU |
| $Al^{3+}$ | From 700 to 790 µg |

Hib is pre-absorbed. The Hib pre-absorbed is mixed with sucrose or lactose prior to freeze drying. The Hib amount will be 2.5 or 5 or 10 µg per human dose. Aluminium content will be from 30 to 120 µg $Al^{3+}$ as $AlPO_4$ per human dose.

The invention claimed is:

1. An inactivated poliovirus (IPV) vaccine comprising:
   (a) diphtheria toxoid;
   (b) tetanus toxoid;
   (c) killed whole-cell *Bordetella pertussis*, substantially thiomersal free; or two or more acellular pertussis components (Pa) and;
   (d) inactivated poliovirus type 1, type 2 and type 3, wherein the inactivated poliovirus type 1 is present at a dose greater than 10 D-antigen units and less than 20 D-antigen units.

2. The vaccine of claim 1, wherein the inactivated poliovirus type 1 is present at 12-18 D-antigen units.

3. The vaccine of claim 1, wherein, the inactivated poliovirus type 3 is present at a dose of 8-20 D-antigen units.

4. The vaccine of claim 1, wherein the inactivated poliovirus type 2 is present at a dose of 2-4 D-antigen units.

5. The vaccine of claim 1, wherein one or more of the diphtheria toxoid, the tetanus toxoid, the killed whole-cell *Bordetella pertussis*, the two or more acellular pertussis components or the inactivated poliovirus type 1 adsorbed onto aluminium hydroxide or aluminium phosphate or a mixture of both.

6. The vaccine of claim 1, additionally comprising Hepatitis B surface antigen, substantially thiomersal free.

7. The vaccine of claim 1, additionally comprising a conjugate of a carrier protein and the capsular saccharide of *Haemophilus influenza* type B (Hib).

8. The vaccine of claim 1, additionally comprising one or more conjugates of a carrier protein and a capsular saccharide of a bacterium selected from the group *Neisseria menigitidis* type A, *Neisseria meningitidis* type C, *Neisseria menigitidis* type W and *Neisseria meningitidis* type Y.

9. The vaccine of claim 1, additionally compromising a *Neisseria meningitidis* type B (MenB) outer membrane vesicle of LOS or a conjugated MenB capsular saccharide.

10. The vaccine of claim 1, additionally comprising a Vi saccharide from *Salmonella typhi* conjugated to a carrier protein.

11. The vaccine of claim 1, additionally comprising an antigen from Hepatitis A.

12. The vaccine of claim 1 wherein the IPV type 1 is from the Mahoney strain.

13. The vaccine claim 1, wherein the IPV type 2 is from the MEF-1 strain.

14. The vaccine, of claim 1, wherein the IPV type 3 is from the Saukett strain.

* * * * *